US007109223B2

(12) United States Patent
Han et al.

(10) Patent No.: US 7,109,223 B2
(45) Date of Patent: Sep. 19, 2006

(54) OXAZOLIDIN-2-ONE AND THIAZOLIDIN-2-ONE DERIVATIVES FOR USE AS $EP_4$ RECEPTOR AGONISTS IN THE TREATMENT OF GLAUCOMA

(75) Inventors: Yongxin Han, Kirkland (CA); John Colucci, Westmount (CA); Xavier Billot, Montreal (CA); Marie-Claire Wilson, Montreal (CA); Robert Young, Senneville (CA)

(73) Assignee: Merck & Co. Inc., Rahway, NJ (US)

( * ) Notice: Subject to any disclaimer, the term of this patent is extended or adjusted under 35 U.S.C. 154(b) by 0 days.

(21) Appl. No.: 10/521,508

(22) PCT Filed: Aug. 25, 2003

(86) PCT No.: PCT/CA03/01306

§ 371 (c)(1),
(2), (4) Date: Jan. 18, 2005

(87) PCT Pub. No.: WO2004/019938

PCT Pub. Date: Mar. 11, 2004

(65) Prior Publication Data

US 2006/0154899 A1    Jul. 13, 2006

Related U.S. Application Data

(60) Provisional application No. 60/406,530, filed on Aug. 28, 2002.

(51) Int. Cl.
*A01N 43/74* (2006.01)
*A01N 43/713* (2006.01)
*A01N 43/76* (2006.01)
*C07D 277/04* (2006.01)
*C07D 257/04* (2006.01)
*C07D 263/04* (2006.01)

(52) U.S. Cl. ............. 514/369; 514/382; 514/376; 548/186; 548/189; 548/253; 548/254; 548/231

(58) Field of Classification Search ........... 548/186, 548/253; 514/369, 382
See application file for complete search history.

(56) References Cited

OTHER PUBLICATIONS

Kubodera, et al. Heterocycles (1982), 18, p. 259-63 (STN search report and abstract).*

* cited by examiner

*Primary Examiner*—Kamal A. Saeed
*Assistant Examiner*—Yong Chu
(74) *Attorney, Agent, or Firm*—Sylvia A. Ayler; Valerie J. Camara

(57) ABSTRACT

This invention relates to potent selective agonists of the $EP_4$ subtype of prostaglandin E2 receptors, their use or a formulation thereof in the treatment of glaucoma and other conditions which are related to elevated intraocular pressure in the eye of a patient. This invention further relates to the use of the compounds of this invention for mediating the bone modeling and remodeling processes of the osteoblasts and osteoclasts.

7 Claims, No Drawings

OXAZOLIDIN-2-ONE AND THIAZOLIDIN-2-ONE DERIVATIVES FOR USE AS EP$_4$ RECEPTOR AGONISTS IN THE TREATMENT OF GLAUCOMA

This Application claims the benefit of U.S. Provisional Application 60/406,530, filed Aug. 28, 2002.

BACKGROUND OF THE INVENTION

Glaucoma is a degenerative disease of the eye wherein the intraocular pressure is too high to permit normal eye function. As a result, damage may occur to the optic nerve head and result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by the majority of ophthalmologists to represent merely the earliest phase in the onset of glaucoma.

Many of the drugs formerly used to treat glaucoma proved unsatisfactory. Early methods of treating glaucoma employed pilocarpine and produced undesirable local effects that made this drug, though valuable, unsatisfactory as a first line drug. More recently, clinicians have noted that many β-adrenergic antagonists are effective in reducing intraocular pressure. While many of these agents are effective for this purpose, there exist some patients with whom this treatment is not effective or not sufficiently effective. Many of these agents also have other characteristics, e.g., membrane stabilizing activity, that become more apparent with increased doses and render them unacceptable for chronic ocular use and can also cause cardiovascular effects.

Agents referred to as carbonic anhydrase inhibitors decrease the formation of aqueous humor by inhibiting the enzyme carbonic anhydrase. While such carbonic anhydrase inhibitors are now used to treat elevated intraocular pressure by systemic and topical routes, current therapies using these agents, particularly those using systemic routes are still not without undesirable effects. Topically effective carbonic anhydrase inhibitors are disclosed in U.S. Pat. Nos. 4,386,098; 4,416,890; 4,426,388; 4,668,697; 4,863,922; 4,797,413; 5,378,703, 5,240,923 and 5,153,192.

Prostaglandins and prostaglandin derivatives are also known to lower intraocular pressure. There are several prostaglandin types, including the A, B, C, D, E, F, G, I and J-Series (EP 0561073 A1). U.S. Pat. No. 4,883,819 to Bito describes the use and synthesis of PGAs, PGBs and PGCs in reducing intraocular pressure. U.S. Pat. No. 4,824,857 to Goh et al. describes the use and synthesis of PGD$_2$ and derivatives thereof in lowering intraocular pressure including derivatives wherein C-10 is replaced with nitrogen. U.S. Pat. No. 5,001,153 to Ueno et al. describes the use and synthesis of 13,14-dihydro-15-keto prostaglandins and prostaglandin derivatives to lower intraocular pressure. U.S. Pat. No. 4,599,353 describes the use of eicosanoids and eicosanoid derivatives including prostaglandins and prostaglandin inhibitors in lowering intraocular pressure. See also WO 00/38667, WO 99/32441, WO 99/02165, WO 00/38663, WO 01/46140, EP 0855389, JP 2000-1472, U.S. Pat. No. 6,043,275 and WO 00/38690.

Prostaglandin and prostaglandin derivatives are known to lower intraocular pressure by increasing uveoscleral outflow. This is true for both the F type and A type of prostaglandins. This invention is particularly interested in those compounds that lower IOP via the uveoscleral outflow pathway and other mechanisms by which the E series prostaglandins (PGE$_2$) may facilitate IOP reduction. The four recognized subtypes of the EP receptor are believed to modulate the effect of lowering IOP (EP$_1$, EP$_2$, EP$_3$ and EP$_4$; J. Lipid Mediators Cell Signaling, Vol. 14, pages 83–87 (1996)). See also J. Ocular Pharmacology, Vol. 4, 1, pages 13–18 (1988); J. Ocular Pharmacology and Therapeutics, Vol. 11, 3, pages 447–454 (1995); J. Lipid Mediators, Vol. 6, pages 545–553 (1993); U.S. Pat. Nos. 5,698,598 and 5,462,968 and Investigative Ophthalmology and Visual Science, Vol. 31, 12, pages 2560–2567 (1990). Of particular interest to this invention are compounds, which are agonist of the EP$_4$ subtype receptor.

A problem with using prostaglandins or derivatives thereof to lower intraocular pressure is that these compounds often induce an initial increase in intraocular pressure, can change the color of eye pigmentation and cause proliferation of some tissues surrounding the eye.

As can be seen, there are several current therapies for treating glaucoma and elevated intraocular pressure, but the efficacy and the side effect profiles of these agents are not ideal. Therefore, there still exist the need for new and effective therapies with little or no side effects.

A variety of disorders in humans and other mammals involve or are associated with abnormal or excessive bone loss. Such disorders include, but are not limited to, osteoporosis, glucocorticoid induced osteoporosis, Paget's disease, abnormally increased bone turnover, periodontal disease, tooth loss, bone fractures, rheumatoid arthritis, periprosthetic osteolysis, osteogenesis imperfecta, metastatic bone disease, hypercalcemia of malignancy, and multiple myeloma. One of the most common of these disorders is osteoporosis, which in its most frequent manifestation occurs in postmenopausal women. Osteoporosis is a systemic skeletal disease characterized by a low bone mass and microarchitectural deterioration of bone tissue, with a consequent increase in bone fragility and susceptibility to fracture. Osteoporotic fractures are a major cause of morbidity and mortality in the elderly population. As many as 50% of women and a third of men will experience an osteoporotic fracture. A large segment of the older population already has low bone density and a high risk of fractures. There is a significant need to both prevent and treat osteoporosis and other conditions associated with bone resorption. Because osteoporosis, as well as other disorders associated with bone loss, are generally chronic conditions, it is believed that appropriate therapy will typically require chronic treatment.

Two different types of cells called osteoblasts and osteoclasts are involved in the bone formation and resorption processes, respectively. See H. Fleisch, *Bisphosphonates In Bone Disease, From The Laboratory To The Patient*, 3rd Edition, Parthenon Publishing (1997), which is incorporated by reference herein in its entirety.

Osteoblasts are cells that are located on the bone surface. These cells secrete an osseous organic matrix, which then calcifies. Substances such as fluoride, parathyroid hormone, and certain cytokines such as protaglandins are known to provide a stimulatory effect on osetoblast cells. However, an aim of current research is to develop therapeutic agents that will selectively increase or stimulate the bone formation activity of the osteoblasts.

Osteoclasts are usually large multinucleated cells that are situated either on the surface of the cortical or trabecular bone or within the cortical bone. The osteoclasts resorb bone in a closed, sealed-off microenvironment located between the cell and the bone. The recruitment and activity of osteoclasts is known to be influenced by a series of cytokines and hormones. It is well known that bisphosphonates are selective inhibitors of osteoclastic bone resorption, making these compounds important therapeutic agents in the treatment or prevention of a variety of systemic or localized bone disorders caused by or associated with abnormal bone resorption. However, despite the utility of bisphosphonates there remains the desire amongst researchers to develop additional therapeutic agents for inhibiting the bone resorption activity of osteoclasts.

Prostaglandins such as the $PGE_2$ series are known to stimulate bone formation and increase bone mass in mammals, including man. It is believed that the four different receptor subtypes, designated $EP_1$, $EP_2$, $EP_3$, and $EP_4$ are involved in mediating the bone modeling and remodeling processes of the osteoblasts and osteoclasts. The major prostaglandin receptor in bone is $EP_4$, which is believed to provide its effect by signaling via cyclic AMP.

In present invention it is further found that the formula I agonists of the $EP_4$ subtype receptor are useful for stimulating bone formation.

WO 02/24647, WO 02/42268, EP 1132086, EP 855389, EP 1114816, WO 01/46140 and WO 01/72268 disclose $EP_4$ agonists.

SUMMARY OF THE INVENTION

This invention relates to potent selective agonists of the $EP_4$ subtype of prostaglandin E2 receptors, their use or a formulation thereof in the treatment of glaucoma and other conditions that are related to elevated intraocular pressure in the eye of a patient. Another aspect of this invention relates to the use of such compounds to provide a neuroprotective effect to the eye of mammalian species, particularly humans. This invention further relates to the use of the compounds of this invention for mediating the bone modeling and remodeling processes of the osteoblasts and osteoclasts.

More particularly, this invention relates to novel EP4 agonist having the structural formula I:

FORMULA I

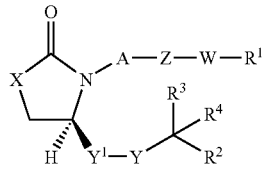

or a pharmaceutically acceptable salt thereof, wherein,
X is O or S;
$Y^1$ is
  1) $CH_2CH_2$,
  2) CHCH, or

3)

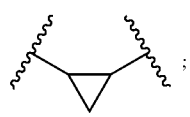

Y is C(O) or CH(OH);

A and W are independently selected from the group consisting of
  1) a bond, and
  2) $C_{1-6}$ alkylene, unsubstituted or substituted with 1, 2, 3, or 4 halogen atoms;
Z is
  1) O,
  2) S,

3)

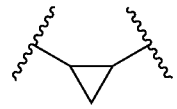

4) $CH_2$
  5) HC=CH,
  6) C≡C, or
  7) a disubstituted aryl or heteroaryl ring, wherein one ring atom of the ring is attached to the moiety

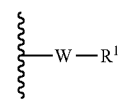

and another ring atom is attached to the moiety

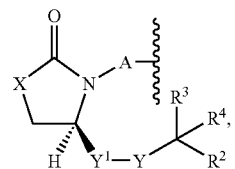

with the proviso that when Z is O or S, then A and W are independently selected from the group consisting of $C_{1-6}$ alkylene, unsubstituted or substituted with 1, 2, 3, or 4 halogen atoms;
$R^1$ is
  $COR^5$,
  OH,
  CN,
  $(CH_2)_{1-3}CO_2R^6$,
  $(CH_2)_{0-4}SO_3R^6$,
  $CF_2SO_2NH_2$,
  $SO_2NH_2$,
  $SO_2NHCOR^8$,
  $PO(OH)_2$,
  $C_{1-4}$ alkoxy,
  hydroxymethylketone,
  $(CH_2)_{0-4}$ heterocyclyl, wherein heterocyclyl is unsubstituted or substituted with 1 to 3 groups of $R^a$, or
  tetrazole;
$R^2$ is
  1) $C_{1-6}$alkyl, provided that $R^2$ is not n-pentyl,
  2) $(CH_2)_{0-8}C_{6-10}$aryl,
  3) $(CH_2)_{0-8}C_{5-10}$heteroaryl,
  4) $(CH_2)_{0-8}C_{3-10}$heterocycloalkyl,
  5) $(CH_2)_{0-8}C_{3-8}$cycloalkyl,
  6) O—$C_{1-10}$alkyl,
  7) O—$C_{6-10}$aryl, 8) O—C$_{5-10}$heteroaryl,
9) O—C$_{5-10}$heterocycloalkyl,
10) O—C$_{3-10}$cycloalkyl
wherein aryl, heteroaryl, heterocycloalkyl, and cycloalkyl are unsubstituted or substituted with 1–3 groups of R$^b$;

R$^3$ and R$^4$ are independently selected from the group consisting of
1) hydrogen,
2) halogen, and
3) C$_{1-6}$ alkyl, or R$^3$ and R$^4$, together with the carbon atom to which they are attached, form a C$_{3-7}$ cycloalkyl ring;

R$^5$ is
1) hydrogen,
2) OH,
3) CH$_2$OH,
4) C$_{1-6}$ alkoxy,
5) NHPO$_2$R$^6$,
6) NHR$^9$,
7) NHSO$_2$R$^8$, or
8) NR$^6$R$^7$;

R$^6$ and R$^7$ are independently selected from the group consisting of hydrogen and C$_{1-6}$ alkyl;

R$^8$ is selected from the group consisting of hydrogen, C$_{6-10}$aryl, and C$_{1-4}$alkyl;

R$^9$ is acyl or sulfonyl; and

R$^a$ and R$^b$ are independently selected from the group consisting of
1) C$_{1-6}$alkoxy,
2) C$_{1-6}$alkyl, unsubstituted or substituted with
    a) C$_{1-6}$ alkoxy,
    b) C$_{1-6}$ alkylthio,
    c) CN,
    d) OH, or
    e) CF$_3$,
3) CF$_3$,
4) nitro,
5) amino,
6) cyano,
7) C$_{1-6}$alkylamino,
8) halogen
9) OR$^c$,
10) OCH$_2$R$^c$, and
11) CH$_2$OR$^c$;

R$^c$ is
1) C$_{6-10}$aryl,
2) C$_{5-10}$heteroaryl,
3) C$_{3-10}$heterocycloalkyl, or
4) C$_{3-8}$cycloalkyl.

The compounds of the present invention may have chiral centers and occur as racemates, racemic mixtures and as individual diastereomers, or enantiomers with all isomeric forms being included in the present invention. The compounds of the present invention may also have polymorphic crystalline forms, with all polymorphic crystalline forms being included in the present invention. The compounds of the invention also include tautomeric forms, with all tautomeric forms being included in the present invention.

The invention also includes prodrug forms of the above-described compounds. Prodrugs, such as ester derivatives of active drug, are compound derivatives which, when absorbed into the bloodstream of a warm-blooded animal, cleave in such a manner as to release the drug form and permit the drug to afford improved therapeutic efficacy. The prodrugs may be administered in low amounts relative to the amounts of antagonist that would ordinarily be administered. The prodrugs may be administered orally. The prodrugs retain structural integrity while passing though the gastrointestinal system, and are effectively delivered to cells. They are subjected to metabolic reactions to form the active acid which then interacts with the platelet receptor site.

This and other aspects of the invention will be realized upon inspection of the invention as a whole.

DETAILED DESCRIPTION OF THE INVENTION

In a class of compounds and pharmaceutically acceptable salts of the invention,

R$^2$ is
1) cyclohexyl,
2) unsubstituted aryl, or
3) aryl substituted with
    a) unsubstituted C$_{1-6}$ alkyl,
    b) C$_{1-6}$ alkyl substituted with C$_{1-6}$ alkoxy
    c) halogen, or
    d) CF$_3$.

In a subclass of this class, R$^1$ is tetrazole or COR$^5$, wherein R$^5$ is CH$_2$OH or OH.

In a group of this subclass, A is a bond, (CH$_2$)$_{1-4}$, or (CH$_2$)$_{1-5}$CF$_2$, and W is a bond or (CH$_2$)$_{1-6}$.

In a subgroup of this group,

Z is
1) CH$_2$,
2) CH=CH,
3) C≡C,
4) O,
5) S,

6) 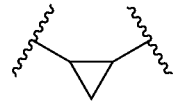

7) disubstituted thiophene,
8) disubstituted furan, or
9) disubstituted benzene; and R$^3$ and R$^4$ are independently selected from the group consisting of hydrogen and F, or R$^3$ and R$^4$, together with the carbon atom to which they are attached, form a cyclopropyl or cyclohexyl ring.

Exemplary compounds of this invention include
7-{4-[(1E)-4,4-difluoro-3-hydroxy-4-phenylbut-1-enyl]-2-oxo-1,3-thiazolidin-3-yl}heptanoic acid,
7-{4-[(1E)-3-hydroxy-4-phenylbut-1-enyl]-2-oxo-1,3-thiazolidin-3-yl}heptanoic acid,
4-[(1E)-4,4-difluoro-3-hydroxy-4-phenylbut-1-enyl]-3-[6-(1H-tetraazol-5-yl)hexyl]-1,3-thiazolidin-2-one,
4-[(1E)-3-hydroxy-4-phenylbut-1-enyl]-3-[6-(1H-tetraazol-5-yl)hexyl]-1,3-thiazolidin-2-one,
4-[(1E)-3-hydroxy-3-(1-phenylcyclopropyl)prop-1-enyl]-3-[6-(1H-tetraazol-5-yl)hexyl]-1,3-thiazolidin-2-one,
4-(3-hydroxy-4-phenylbutyl)-3-[6-(1H-tetraazol-5-yl)hexyl]-1,3-thiazolidin-2-one,
4-(4,4-difluoro-3-hydroxy-4-phenylbutyl)-3-[6-(1H-tetraazol-5-yl)hexyl]-1,3-thiazolidin-2-one,
7-(4-{(1E)-4,4-difluoro-3-hydroxy-4-[3-(methoxymethyl)phenyl]but-1-enyl}-2-oxo-1,3-thiazolidin-3-yl)heptanoic acid, 4-{(1E)-4,4-difluoro-3-hydroxy-4-[3-(methoxymethyl)phenyl]but-1-enyl}-3-[6-(1H-tetraazol-5-yl)hexyl]-1,3-thiazolidin-2-one, 4-[(1E)-4-cyclohexyl-4,4-difluoro-3-hydroxybut-1-enyl]-3-[6-(1H-tetraazol-5-yl)hexyl]-1,3-thiazolidin-2-one, 4-[(1E)-4-cyclohexyl-3-hydroxybut-1-enyl]-3-[6-(1H-tetraazol-5-yl)hexyl]-1,3-thiazolidin-2-one, 4-(4,4-difluoro-3-oxo-4-phenylbutyl)-3-[6-(1H-tetraazol-5-yl)hexyl]-1,3-thiazolidin-2-one, 4-(3-oxo-4-phenylbutyl)-3-[6-(1H-tetraazol-5-yl)hexyl]-1,3-thiazolidin-2-one, 4-[2-(2,2-difluoro-1-hydroxy-2-phenylethyl)cyclopropyl]-3-[6-(1H-tetraazol-5-yl)hexyl]-1,3-thiazolidin-2-one, 4-[2-(1-hydroxy-2-phenylethyl)cyclopropyl]-3-[6-(1H-tetraazol-5-yl)hexyl]-1,3-thiazolidin-2-one, 4-[2-(1-hydroxy-2-phenylethyl)cyclopropyl]-3-[6-(1H-tetraazol-5-yl)hexyl]-1,3-thiazolidin-2-one, 4-[(1E)-4,4-difluoro-3-hydroxy-4-phenylbut-1-enyl]-3-(7-hydroxy-6-oxoheptyl)-1,3-thiazolidin-2-one, 4-[(1E)-4,4-difluoro-3-hydroxy-4-phenylbut-1-enyl]-3-[(2E)-6-(1H-tetraazol-5-yl)hex-2-enyl]-1,3-thiazolidin-2-one, 4-[(1E)-4,4-difluoro-3-hydroxy-4-phenylbut-1-enyl]-3-[(3E)-6-(1H-tetraazol-5-yl)hex-3-enyl]-1,3-thiazolidin-2-one, 4-[(1E)-4,4-difluoro-3-hydroxy-4-phenylbut-1-enyl]-3-[(4E)-6-(1H-tetraazol-5-yl)hex-4-enyl]-1,3-thiazolidin-2-one, 4-[(1E)-4,4-difluoro-3-hydroxy-4-phenylbut-1-enyl]-3-[(2Z)-6-(1H-tetraazol-5-yl)hex-2-enyl]-1,3-thiazolidin-2-one, 4-[(1E)-4,4-fluoro-3-hydroxy-4-phenylbut-1-enyl]-3-[(3Z)-6-(1H-tetraazol-5-yl)hex-3-enyl]-1,3-thiazolidin-2-one, 4-[(1E)-4,4-difluoro-3-hydroxy-4-phenylbut-1-enyl]-3-[(4Z)-6-(1H-tetraazol-5-yl)hex-4-enyl]-1,3-thiazolidin-2-one, 4-[(1E)-4,4-difluoro-3-hydroxy-4-phenylbut-1-enyl]-3-[6-(1H-tetraazol-5-yl)hex-4-ynyl]-1,3-thiazolidin-2-one, 4-[(1E)-4,4-difluoro-3-hydroxy-4-phenylbut-1-enyl]-3-[6-(H-tetraazol-5-yl)hex-2-ynyl]-1,3-thiazolidin-2-one, 4-[(1E)-4,4-difluoro-3-hydroxy-4-phenylbut-1-enyl]-3-[6-(1H-tetraazol-5-yl)hex-3-ynyl]-1,3-thiazolidin-2-one, 5-(3-{4-[(1E)-4,4-difluoro-3-hydroxy-4-phenylbut-1-enyl]-2-oxo-1,3-thiazolidin-3-yl}propyl)thiophene-2-carboxylic acid, 5-(3-{4-[(1E)-4,4-difluoro-3-hydroxy-4-phenylbut-1-enyl]-2-oxo-1,3-thiazolidin-3-yl}propyl)-2-furoic acid, 4-[(1E)-4,4-difluoro-3-hydroxy-4-phenylbut-1-enyl]-3-{3-[5-(1H-tetraazol-5-yl)-2-furyl]propyl}-1,3-thiazolidin-2-one, 4-[(1E)-4,4-difluoro-3-hydroxy-4-phenylbut-1-enyl]-3-{3-[5-(1H-tetraazol-5-yl)thien-2-yl]propyl}-1,3-thiazolidin-2-one, 4-[(1E)-4,4-difluoro-3-hydroxy-4-phenylbut-1-enyl]-3-{(2E)-3-[5-(1H-tetraazol-5-yl)thien-2-yl]prop-2-enyl}-1,3-thiazolidin-2-one, 4-[(1E)-4,4-difluoro-3-hydroxy phenylbut-1-enyl]-3-{(2E)-3-[5-(1H-tetraazol-5-yl)-2-furyl]prop-2-enyl}-1,3-thiazolidin-2-one, 4-[(-4,4-difluoro-3-hydroxy-4-phenylbut-1-enyl]-3-{(2Z)-3-[5-(1H-tetraazol-5-yl)thien-2-yl]prop-2-enyl}-1,3-thiazolidin-2-one, 4-[(1E)-4,4-difluoro-3-hydroxy-4-phenylbut-1-enyl]-3-{(2Z)-3-[5-(1H-tetraazol-5-yl)-2-furyl]prop-2-enyl}-1,3-thiazolidin-2-one, 3-(3-{4-[(1E)-4,4-difluoro-3-hydroxy-4-phenylbut-1-enyl]-2-oxo-1,3-thiazolidin-3-yl}propyl)benzoic acid, 4-(3-{4-[(1E)-4,4-difluoro-3-hydroxy-4-phenylbut-1-enyl]-2-oxo-1,3-thiazolidin-3-yl}propyl)benzoic acid, 2-(3-{4-[(1E)-4,4-difluoro-3-hydroxy-4-phenylbut-1-enyl]-2-oxo-1,3-thiazolidin-3-yl}propyl)benzoic acid, 4-[(1E)-4,4-difluoro-3-hydroxy-4-phenylbut-1-enyl]-3-{3-[3-(1H-tetraazol-5-yl)phenyl]propyl}-1,3-thiazolidin-2-one, 4-[(1E)-4,4-difluoro-3-hydroxy-4-phenylbut-1-enyl]-3-{3-[2-(1H-tetraazol-5-yl)phenyl]propyl}-1,3-thiazolidin-2-one, 4-[(1E)-4,4-difluoro-3-hydroxy-4-phenylbut-1-enyl]-3 {3-[4-(H-tetraazol-5-yl)phenyl]propyl}-1,3-thiazolidin-2-one, 4-[(1E)-4,4-difluoro-3-hydroxy-4-phenylbut-1-enyl]-3-{2-[3-(1H-tetraazol-5-ylmethyl)phenyl]ethyl}-1,3-thiazolidin-2-one, 4-[(1E)-4,4-difluoro-3-hydroxy-4-phenylbut-1-enyl]-3-{2-[4-(1H-tetraazol-5-ylmethyl)phenyl]ethyl}-1,3-thiazolidin-2-one, 4-[(1E)-4,4-difluoro-3-hydroxy-4-phenylbut-1-enyl]-3-{2-[2-(1H-tetraazol-5-ylmethyl)phenyl]ethyl}-1,3-thiazolidin-2-one, 7-{4-[(1E)-4,4-difluoro-3-hydroxy-4-phenylbut-1-enyl]-2-oxo-1,3-thiazolidin-3-yl}-2,2-difluoroheptanoic acid, 7-{4-[(1E)-4,4-difluoro-3-hydroxy-4-phenylbut-1-enyl]-2-oxo-1,3-thiazolidin-3-yl}-4,4-difluoroheptanoic acid, 7-{4-[(1E)-4,4-difluoro-3-hydroxy-4-phenylbut-1-enyl]-2-oxo-1,3-thiazolidin-3-yl}-5,5-difluoroheptanoic acid, 7-{4-[(1E)-4,4-difluoro-3-hydroxy-4-phenylbut-1-enyl]-2-oxo-1,3-thiazolidin-3-yl}-6,6-difluoroheptanoic acid, 4-(2-{4-[(1E)-4,4-difluoro-3-hydroxy-4-phenylbut-1-enyl]-2-oxo-1,3-thiazolidin-3-yl}ethoxy)butanoic acid, 3-(3-{4-[(1E)-4,4-difluoro-3-hydroxy-4-phenylbut-1-enyl]-2-oxo-1,3-thiazolidin-3-yl}propoxy)propanoic acid, (4-{4-[(1E)-4,4-difluoro-3-hydroxy-4-phenylbut-1-enyl]-2-oxo-1,3-thiazolidin-3-yl}butoxy)acetic acid,

[(4-{4-[(1E)-4,4-difluoro-3-hydroxy-4-phenylbut-1-enyl]-2-oxo-1,3-thiazolidin-3-yl}butyl)thio]acetic acid, 3-[(3-{4-[(1E)-4,4-difluoro-3-hydroxy-4-phenylbut-1-enyl]-2-oxo-1,3-thiazolidin-3-yl}propyl)thio]propanoic acid, 4-[(2-{4-[(1E)-4,4-difluoro-3-hydroxy-4-phenylbut-1-enyl]-2-oxo-1,3-thiazolidin-3-yl}ethyl)thio]butanoic acid, 7-{4-[(1E)-4,4-difluoro-3-hydroxy-4-phenylbut-1-enyl]-2-oxo-1,3-oxazolidin-3-yl}heptanoic acid, 7-{4-[(1E)-3-hydroxy-4-phenylbut-1-enyl]-2-oxo-1,3-oxazolidin-3-yl}heptanoic acid, 4-[(1E)-4,4-difluoro-3-hydroxy-4-phenylbut-1-enyl]-3-[6-(1H-tetraazol-5-yl)hexyl]-1,3-oxazolidin-2-one, 4-[(1E)-3-hydroxy-4-phenylbut-1-enyl]-3-[6-(1H-tetraazol-5-yl)hexyl]-1,3-oxazolidin-2-one, 4-[(1E)-3-hydroxy-3-(1-phenylcyclopropyl)prop-1-enyl]-3-[6-(1H-tetraazol-5-yl)hexyl]-1,3-oxazolidin-2-one, 4-(3-hydroxy-4-phenylbutyl)-3-[6-(1H-tetraazol-5-yl)hexyl]-1,3-oxazolidin-2-one, 4-(4,4-difluoro-3-hydroxy-4-phenylbutyl)-3-[6-(H-tetraazol-5-yl)hexyl]-1,3-oxazolidin-2-one, 7-(4-{(1E)-4,4-difluoro-3-hydroxy-4-[3-(methoxymethyl)phenyl]but-1-enyl}-2-oxo-1,3-oxazolidin-3-yl)heptanoic acid, 4-{(1E)-4,4-difluoro-3-hydroxy-4-[3-(methoxymethyl)phenyl]but-1-enyl}-3-[6-(1H-tetraazol-5-yl)hexyl]-1,3-oxazolidin-2-one, 4-[(1E)-4-cyclohexyl-4,4-difluoro-3-hydroxybut-1-enyl]-3-[6-(1H-tetraazol-5-yl)hexyl]-1,3-oxazolidin-2-one, 4-[(1E)-4-cyclohexyl-3-hydroxybut-1-enyl]-3-[6-(1H-tetraazol-5-yl)hexyl]-1,3-oxazolidin-2-one,
4-(4,4-difluoro-3-oxo-4-phenylbutyl)-3-[6-(1H-tetraazol-5-yl)hexyl]-1,3-oxazolidin-2-one,
4-(3-oxo-4-phenylbutyl)-3-[6-(1H-tetraazol-5-yl)hexyl]-1,3-oxazolidin-2-one,
4-[2-(2,2-difluoro-1-hydroxy-2-phenylethyl)cyclopropyl]-3-[6-(1H-tetraazol-5-yl)hexyl]-1,3-oxazolidin-2-one,
4-[2-(1-hydroxy-2-phenylethyl)cyclopropyl]-3-[6-(1H-tetraazol-5-yl)hexyl]-1,3-oxazolidin-2-one,
4-[2-(1-hydroxy-2-phenylethyl)cyclopropyl]-3-[6-(1H-tetraazol-5-yl)hexyl]-1,3-oxazolidin-2-one,
4-[(1E)-4,4-difluoro-3-hydroxy-4-phenylbut-1-enyl]-3-(7-hydroxy-6-oxoheptyl)-1,3-oxazolidin-2-one,
4-[(1E)-4,4-difluoro-3-hydroxy-4-phenylbut-1-enyl]-3-[(2E)-6-(1H-tetraazol-5-yl)hex-2-enyl]-1,3-oxazolidin-2-one,
4-[(1E)-4,4-difluoro-3-hydroxy-4-phenylbut-1-enyl]-3-[(3E)-6-(1H-tetraazol-5-yl)hex-3-enyl]-1,3-oxazolidin-2-one,
4-[(1E)-4,4-difluoro-3-hydroxy-4-phenylbut-1-enyl]-3-[(4E)-6-(1H-tetraazol-5-yl)hex-4-enyl]-1,3-oxazolidin-2-one,
4-[(1E)-4,4-difluoro-3-hydroxy-4-phenylbut-1-enyl]-3-[(2Z)-6-(1H-tetraazol-5-yl)hex-2-enyl]-1,3-oxazolidin-2-one,
4-[(1E)-4,4-difluoro-3-hydroxy-4-phenylbut-1-enyl]-3-[(3Z)-6-(1H-tetraazol-5-yl)hex-3-enyl]-1,3-oxazolidin-2-one,
4-[(1E)-4,4-difluoro-3-hydroxy-4-phenylbut-1-enyl]-3-[(4Z)-6-(1H-tetraazol-5-yl)hex-4-enyl]-1,3-oxazolidin-2-one,
4-[(1E)-4,4-difluoro-3-hydroxy-4-phenylbut-1-enyl]-3-[6-(1H-tetraazol-5-yl)hex 4-ynyl]-1,3-oxazolidin-2-one,
4-[(1E)-4,4-difluoro-3-hydroxy-4-phenylbut-1-enyl]-3-[6-(1H-tetraazol-5-yl)hex-2-ynyl]-1,3-oxazolidin-2-one,
4-[(1E)-4,4-difluoro-3-hydroxy-4-phenylbut-1-enyl]-3-[6-(1H-tetraazol-5-yl)hex-3-ynyl]-1,3-oxazolidin-2-one,
5-(3-{4-[(1E)-4,4-difluoro-3-hydroxy-4-phenylbut-1 enyl]-2-oxo-1,3-oxazolidin-3-yl}propyl)thiophene-2-carboxylic acid,
5-(3-{4-[(1E)-4,4-difluoro-3-hydroxy-4-phenylbut-1-enyl]-2-oxo-1,3-oxazolidin-3-yl}propyl)-2-furoic acid,
4-[(1E)-4,4-difluoro-3-hydroxy-4-phenylbut-1-enyl]-3-{3-[5-(1H-tetraazol-5-yl)-2-furyl]propyl}-1,3-oxazolidin-2-one,
4-[(1E)-4,4-difluoro-3-hydroxy-4-phenylbut-1-enyl]-3-{3-[5-(1H-tetraazol-5-yl)thien-2-yl]propyl}-1,3-oxazolidin-2-one,
4-[(1E)-4,4-difluoro-3-hydroxy-4-phenylbut-1-enyl]-3-{(2E)-3-[5-(1H-tetraazol-5-yl)thien-2-yl]prop-2-enyl}-1,3-oxazolidin-2-one,
4-[(1E)-4,4-difluoro-3-hydroxy-4-phenylbut-1-enyl]-3-{(2E)-3-[5-(1H-tetraazol-5-yl)-2-furyl]prop-2-enyl}-1,3-oxazolidin-2-one,
4-[(1E)-4,4-difluoro-3-hydroxy-4-phenylbut-1-enyl]-3-{(2E)-3-[5-(1H-tetraazol-5-yl)thien-2-yl]prop-2-enyl}-1,3-oxazolidin-2-one,
4-[(1E)-4,4-difluoro-3-hydroxy-4-phenylbut-1-enyl]-3-{(2E)-3-[5-(1H-tetraazol-5-yl)-2-furyl]prop-2-enyl}-1,3-oxazolidin-2-one,
3-(3-{4-[(1E)-4,4-difluoro-3-hydroxy-4-phenylbut-1-enyl]-2-oxo-1,3-oxazolidin-3-yl}propyl)benzoic acid,
4-(3-{4-[(1E)-4,4-difluoro-3-hydroxy-4-phenylbut-1-enyl]-2-oxo-1,3-oxazolidin-3-yl}propyl)benzoic acid,
2-(3-{4-[(1E)-4,4-difluoro-3-hydroxy phenylbut-1-enyl]-2-oxo-1,3-oxazolidin-3-yl}propyl)benzoic acid,
4-[(1E)-4,4-difluoro-3-hydroxy-4-phenylbut-1-enyl]-3-{3-[3-(1H-tetraazol-5-yl)phenyl]propyl}-1,3-oxazolidin-2-one,
4-[(1E)-4,4-difluoro-3-hydroxy-4-phenylbut-1-enyl]-3-{3-[2-(1H-tetraazol-5-yl)phenyl]propyl}-1,3-oxazolidin-2-one,
4-[(1E)-4,4-difluoro-3-hydroxy-4-phenylbut-1-enyl]-3-{3-[4-(1H-tetraazol-5-yl)phenyl]propyl}-1,3-oxazolidin-2-one,
4-[(1E)-4,4-difluoro-3-hydroxy-4-phenylbut-1-enyl]-3-{2-[3-(1H-tetraazol-5-ylmethyl)phenyl]ethyl}-1,3-oxazolidin-2-one,
4-[(1E)-4,4-difluoro-3-hydroxy-4-phenylbut-1-enyl]-3-{2-[4-(1H-tetraazol-5-ylmethyl)phenyl]ethyl}-1,3-oxazolidin-2-one,
4-[(1E)-4,4-difluoro-3-hydroxy-4-phenylbut-1-enyl]-3-{2-[2-(1H-tetraazol-5-ylmethyl)phenyl]ethyl}-1,3-oxazolidin-2-one,
7-{4-[(1E)-4,4-difluoro-3-hydroxy-4-phenylbut-1-enyl]-2-oxo-1,3-oxazolidin-3-yl}-2,2-difluoroheptanoic acid,
7-{4-[(1E)-4,4-difluoro-3-hydroxy-4-phenylbut-1-enyl]-2-oxo-1,3-oxazolidin-3-yl}-4,4-difluoroheptanoic acid,
7-{4-[(1E)-4,4-difluoro-3-hydroxy-4-phenylbut-1-enyl]-2-oxo-1,3-oxazolidin-3-yl}-5,5-difluoroheptanoic acid,
7-{4-[(1E)-4,4-difluoro-3-hydroxy-4-phenylbut-1-enyl]-2-oxo-1,3-oxazolidin-3-yl}-6,6-difluoroheptanoic acid,
4-(2-{4-[(1E)-4,4-difluoro-3-hydroxy-4-phenylbut-1-enyl]-2-oxo-1,3-oxazolidin-3-yl}ethoxy)butanoic acid,
3-(3-{4-[(1E)-4,4-difluoro-3-hydroxy-4-phenylbut-1-enyl]-2-oxo-1,3-oxazolidin-3-yl}propoxy)propanoic acid,
(4-{4-[(1E)-4,4-difluoro-3-hydroxy-4-phenylbut-1-enyl]-2-oxo-1,3-oxazolidin-3-yl}butoxy)acetic acid,
[(4-{4-[(1E)-4,4-difluoro-3-hydroxy-4-phenylbut-1-enyl]-2-oxo-1,3-oxazolidin-3-yl}butyl)thio]acetic acid,
3-[(3-{4-[(1E)-4,4-difluoro-3-hydroxy-4-phenylbut-1-enyl]-2-oxo-1,3-oxazolidin-3-yl}propyl)thio]propanoic acid,
4-[(2-{4-[(1E)-4,4-difluoro-3-hydroxy-4-phenylbut-1-enyl]-2-oxo-1,3-oxazolidin-3-yl}ethyl)thio]butanoic acid, and pharmaceutically acceptable salts thereof.

The invention is described herein in detail using the terms defined below unless otherwise specified.

The term "therapeutically effective amount", as used herein, means that amount of the $EP_4$ receptor subtype agonist of formula I, or other actives of the present invention, that will elicit the desired therapeutic effect or response or provide the desired benefit when administered in accordance with the desired treatment regimen. A preferred therapeutically effective amount relating to the treatment of abnormal bone resorption is a bone formation, stimulating amount. Likewise, a preferred therapeutically effective amount relating to the treatment of ocular hypertension or glaucoma is an amount effective for reducing intraocular pressure and/or treating ocular hypertension and/or glaucoma.

The term "pharmaceutically acceptable" as used herein, means generally suitable for administration to a mammal, including humans, from a toxicity or safety standpoint.

The term "prodrug" refers to compounds which are drug precursors which, following administration and absorption, release the claimed drug in vivo via some metabolic process. A non-limiting example of a prodrug of the compounds of this invention would be an acid of the pyrrolidinone group, where the acid functionality has a structure that makes it easily hydrolyzed after administration to a patient. Exemplary prodrugs include acetic acid derivatives that are non-narcotic, analgesics/non-steroidal, anti-inflammatory drugs having a free CH$_2$COOH group (which can optionally be in the form of a pharmaceutically acceptable salt, e.g. —CH$_2$COO—Na+), typically attached to a ring system, preferably to an aromatic or heteroaromatic ring system.

The term "alkyl", unless otherwise specified, refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl. When the alkyl group is said to be substituted with an alkyl group, this is used interchangeably with "branched alkyl group".

The term "alkoxy" refers to C$_1$–C$_6$ alkyl-O—, with the alkyl group optionally substituted as described herein. Examples of alkoxy groups are methoxy, ethoxy, propoxy, butoxy and isomeric groups thereof.

The terms "halogen" or "halo" refer to chlorine, fluorine, iodine or bromine.

The term "aryl" refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Unless otherwise specified, the aryl ring can be unsubstituted or substituted with one or more of —CF$_3$, —CN, C$_{1-4}$ alkyl, hydroxy, C$_{1-4}$ alkoxy, halogen, e.g. F, Cl, Br, or I, —NO$_2$, —NR$^d$R$^f$, —SO$_2$R$^d$, SO$_2$NR$^d$R$^f$, —CONR$^d$R$^f$, or COR$^d$, wherein R$^d$ and R$^f$ are independently selected hydrogen and C$_{1-4}$ alkyl. Preferred substituted aryls include phenyl and naphthyl.

The term "heterocycloalkyl" refers to a cycloalkyl group (nonaromatic) having 3 to 10 carbon atoms in which one of the carbon atoms in the ring is replaced by a heteroatom selected from O, S or N, and in which up to three additional carbon atoms may be replaced by hetero atoms. Unless otherwise specified, the heterocycloalkyl ring can be unsubstituted or substituted with one or more of C$_{1-4}$ alkyl, hydroxy, C$_{1-4}$ alkoxy, amino, and halogen, e.g. F, Cl, Br, or I.

The term "cycloalkyl", unless otherwise specified, refers to a cyclic alkyl group (nonaromatic) having the specified number of carbon atoms, e.g., C$_{3-7}$ cycloalkyl has 3, 4, 5, 6, or 7 carbon atoms. Unless otherwise specified, the cycloalkyl ring can be unsubstituted or substituted with one or more of C$_{1-4}$ alkyl, hydroxy, C$_{1-4}$ alkoxy, amino, and halogen, e.g. F, Cl, Br, or I. Examples include cyclopropyl, cyclobutyl, and cyclopentyl.

The term "heteroatom" means O, S or N, selected on an independent basis.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of this type are pyrrole, pyridine, oxazole, thiazole, tetrazole, and oxazine. Unless otherwise specified, the heteraryl ring can be unsubstituted or substituted with one or more of C$_{1-4}$ alkyl, hydroxy, C$_{1-4}$ alkoxy, amino, and halogen, e.g. F, Cl, Br, or I. For purposes of this invention the tetrazole includes all tautomeric forms. Additional nitrogen atoms may be present together with the first nitrogen and oxygen or sulfur, giving, e.g., thiadiazole.

The terms "heterocyclyl" and "heterocyclic", as used herein, represent a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. A fused heterocyclic ring system may include carbocyclic rings and need include only one heterocyclic ring. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl. An embodiment of the examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, 2-pyridinonyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl. Unless otherwise specified, the hetercyclyl ring can be unsubstituted or substituted with one or more of C$_{1-4}$ alkyl, hydroxy, C$_{1-4}$ alkoxy, amino, and halogen, e.g. F, Cl, Br, or I.

The term "a disubstituted aryl or heteroaryl ring" includes aryl and heteroaryl rings in which two ring carbon atoms have substituents attached and do not have hydrogen atoms attached, e.g. 2,5-substituted thiophene, furan, and thiazole, and 1,2-, 1,3- and 1,4-substituted benzene. Such disubstituted rings include, but are not limited to, those structurally depicted as

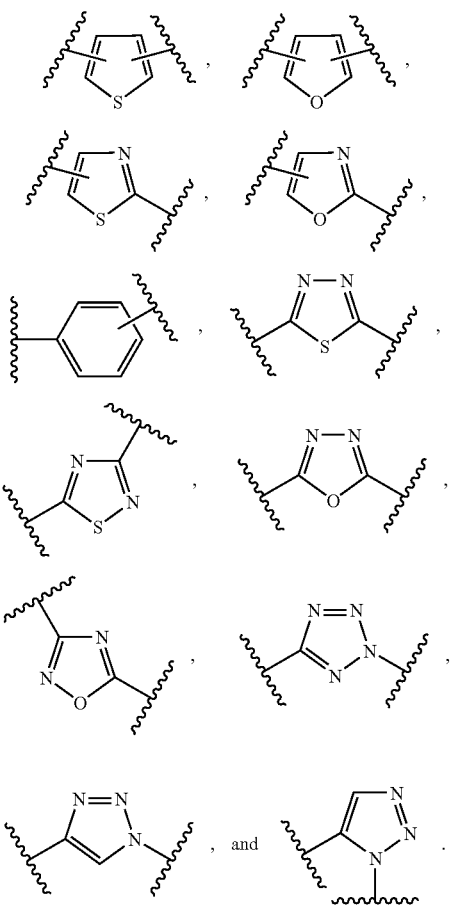

In a preferred embodiment, the disubstituted aryl ring is

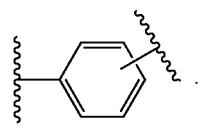

In another preferred embodiment, the disubstituted heteroaryl ring is

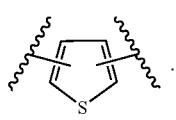

In another preferred embodiment, the disubstituted heteroaryl ring is

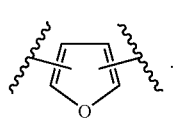

In another preferred embodiment, the disubstituted heteroaryl ring is

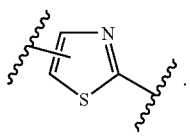

In another preferred embodiment, the disubstituted heteroaryl ring is

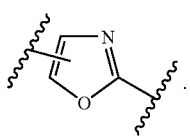

In another preferred embodiment, the disubstituted heteroaryl ring is

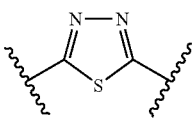

In another preferred embodiment, the disubstituted heteroaryl ring is

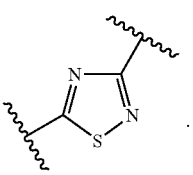

In another preferred embodiment, the disubstituted heteroaryl ring is

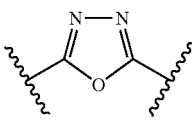

In another preferred embodiment, the disubstituted heteroaryl ring is

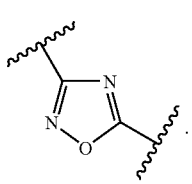

In another preferred embodiment, the disubstituted heteroaryl ring is

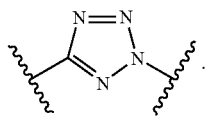

In another preferred embodiment, the disubstituted heteroaryl ring is

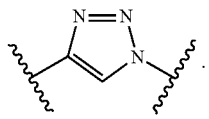

In another preferred embodiment, the disubstituted heteroaryl ring is

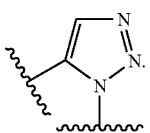

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

The term "agonist" as used herein means $EP_4$ subtype compounds of formula I interact with the EP4 receptor to produce maximal, super maximal or submaximal effects compared to the natural agonist, PGE2. See Goodman and Gilman, The Pharmacological Basis of Therapeutics, $9^{th}$ edition, 1996, chapter 2.

Another embodiment of this invention is directed to a composition containing an $EP_4$ agonist of Formula I and optionally a pharmaceutically acceptable carrier.

Yet another embodiment of this invention is directed to a method for decreasing elevated intraocular pressure or treating glaucoma by administration, preferably topical or intracamaral administration, of a composition containing an $EP_4$ agonist of Formula I and optionally a pharmaceutically acceptable carrier. Use of the compounds of formula I for the manufacture of a medicament for treating elevated intraocular pressure or glaucoma or a combination thereof is also included in this invention.

This invention is further concerned with a process for making a pharmaceutical composition comprising a compound of formula I.

This invention is further concerned with a process for making a pharmaceutical composition comprising a compound of formula I, and a pharmaceutically acceptable carrier.

The claimed compounds bind strongly and act on $PGE_2$ receptor, particularly on the $EP_4$ subtype receptor and therefore are useful for preventing and/or treating glaucoma and ocular hypertension.

Dry eye is a common ocular surface disease afflicting millions of people. Although it appears that dry eye may result from a number of unrelated pathogenic causes, the common end result is the breakdown of the tear film, which results in dehydration of the exposed outer surface of the eye. (Lemp, Report of the Nation Eye Institute/Industry Workshop on Clinical Trials in Dry Eyes, The CLAO Journel, 21(4):221–231 (1995)). One cause for dry eye is the decreased mucin production by the conjunctival cells and/or corneal epithelial cells of mucin, which protects and lubricates the ocular surface (Gipson and Inatomi, Mucin genes expressed by ocular surface epithelium. Progress in Retinal and Eye Research, 16:81–98 (1997)). Functional EP4 receptors have been found in human conjuctival epithelial cells (see U.S. Pat. No. 6,344,477, incorporated by reference in its entirey) and it is appreciated that both human corneal epithelial cells (Progess in Retinal and Eye Research, 16:81–98(1997)) and conjuctival cells (Dartt et al. Localization of nerves adjacent to goblet cells in rat conjucntiva. Current Eye Research, 14:993–1000 (1995)) are capable of secreting mucins. Thus, the compounds of formula I are useful for treating dry eye.

Macular edema is swelling within the retina within the critically important central visual zone at the posterior pole of the eye. An accumulation of fluid within the retina tends to detach the neural elements from one another and from their local blood supply, creating a dormancy of visual function in the area. It is believed that $EP_4$ agonist which lower IOP are useful for treating diseases of the macular such as macular edema or macular degeneration. Thus, another aspect of this invention is a method for treating macular edema or macular degeneration.

Glaucoma is characterized by progressive atrophy of the optic nerve and is frequently associated with elevated intraocular pressure (IOP). It is possible to treat glaucoma, however, without necessarily affecting IOP by using drugs that impart a neuroprotective effect. See Arch. Ophthalmol. Vol. 112, January 1994, pp. 37–44; Investigative Ophthamol. & Visual Science, 32, 5, April 1991, pp. 1593–99. It is believed that $EP_4$ agonist which lower IOP are useful for providing a neuroprotective effect. They are also believed to be effective for increasing retinal and optic nerve head blood velocity and increasing retinal and optic nerve oxygen by lowering IOP, which when coupled together benefits optic nerve health. As a result, this invention further relates to a method for increasing retinal and optic nerve head blood velocity, or increasing retinal and optic nerve oxygen tension or providing a neuroprotective effect or a combination thereof by using an $EP_4$ agonist of formula I.

The compounds produced in the present invention are readily combined with suitable and known pharmaceutically acceptable excipients to produce compositions which may be administered to mammals, including humans, to achieve effective IOP lowering. Thus, this invention is also concerned with a method of treating ocular hypertension or glaucoma by administering to a patient in need thereof one of the compounds of formula I alone or in combination with a β-adrenergic blocking agent such as timolol, betaxolol, levobetaxolol, carteolol, levobunolol, a parasympathomimetic agent such as pilocarpine, a sympathomimetic agents such as epinephrine, iopidine, brimonidine, clonidine, para-aminoclonidine, a carbonic anhydrase inhibitor such as dorzolamide, acetazolamide, metazolamide or brinzolamide; a prostaglandin such as latanoprost, travaprost, unoprostone, rescula, S1033 (compounds set forth in U.S. Pat. Nos. 5,889,052; 5,296,504; 5,422,368; and 5,151,444); a hypotensive lipid such as lumigan and the compounds set forth in U.S. Pat. No. 5,352,708; a neuroprotectant disclosed in U.S. Pat. No. 4,690,931, particularly eliprodil and R-eliprodil as set forth in WO 94/13275, including memantine; or an agonist of 5-HT2 receptors as set forth in PCT/US00/31247, particularly 1-(2-aminopropyl)-3-methyl-1H-imdazol-6-ol fumarate and 2-(3-chloro-6-methoxy-indazol-1-yl)-1-methyl-ethylamine.

This invention is also concerned with a method for increasing retinal and optic nerve head blood velocity, or increasing retinal and optic nerve oxygen tension or providing a neuroprotective effect or a combination thereof by administering to a patient in need thereof one of the compounds of formula I alone or in combination with a β-adrenergic blocking agent such as timolol, betaxolol, levobetaxolol, carteolol, levobunolol, a parasympathomimetic agent such as pilocarpine, a sympathomimetic agents such as epinephrine, iopidine, brimonidine, clonidine, para-aminoclonidine, a carbonic anhydrase inhibitor such as dorzolamide, acetazolamide, metazolamide or brinzolamide; a prostaglandin such as latanoprost, travaprost, unoprostone, rescula, S1033 (compounds set forth in U.S. Pat. Nos. 5,889,052; 5,296,504; 5,422,368; and 5,151,444); a hypotensive lipid such as lumigan and the compounds set forth in U.S. Pat. No. 5,352,708; a neuroprotectant disclosed in U.S. Pat. No. 4,690,931, particularly eliprodil and R-eliprodil as set forth in WO 94/13275, including memantine; or an agonist of 5-HT2 receptors as set forth in PCT/US00/31247, particularly 1-(2-aminopropyl)-3-methyl-1H-imdazol-6-ol fumarate and 2-(3-chloro-6-methoxy-indazol-1-yl)-1-methyl-ethylamine. Use of the compounds of formula I for the manufacture of a medicament for increasing retinal and optic nerve head blood velocity, or increasing retinal and optic nerve oxygen tension or providing a neuroprotective effect or a combination thereof is also included in this invention.

This invention is further concerned with a method for treating macular edema or macular degeneration by administering to a patient in need thereof one of the compounds of formula I alone or in combination with a β-adrenergic blocking agent such as timolol, betaxolol, levobetaxolol, carteolol, levobunolol, a parasympathomimetic agent such as pilocarpine, a sympathomimetic agents such as epinephrine, iopidine, brimonidine, clonidine, para-aminoclonidine, a carbonic anhydrase inhibitor such as dorzolamide, acetazolamide, metazolamide or brinzolamide; a prostaglandin such as latanoprost, travaprost, unoprostone, rescula, S1033 (compounds set forth in U.S. Pat. Nos. 5,889,052; 5,296,504; 5,422,368; and 5,151,444); a hypotensive lipid such as lumigan and the compounds set forth in U.S. Pat. No. 5,352,708; a neuroprotectant disclosed in U.S. Pat. No. 4,690,931, particularly eliprodil and R-eliprodil as set forth in WO 94/13275, including memantine; or an agonist of 5-HT2 receptors as set forth in PCT/US00/31247, particularly 1-(2-aminopropyl)-3-methyl-1H-imdazol-6-ol fumarate and 2-(3-chloro-6-methoxy-indazol-1-yl)-1-methyl-ethylamine: Use of the compounds of formula I for the manufacture of a medicament for macular edema or macular degeneration is also included in this invention.

Compounds of the invention may also be used to treat neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitate them. Neuropathic pain syndromes include: diabetic neuropathy; sciatica; non-specific lower back pain; multiple sclerosis pain; fibromyalgia; HIV-related neuropathy, post-herpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Compounds of the invention may also be used to treat acute renal failure, chronic renal failure, colon cancer, colitis, and HIV latency.

The $EP_4$ agonist used in the instant invention can be administered in a therapeutically effective amount intravaneously, subcutaneously, topically, transdermally, parenterally or any other method known to those skilled in the art. Ophthalmic pharmaceutical compositions are preferably adapted for topical administration to the eye in the form of solutions, suspensions, ointments, creams or as a solid insert. Ophthalmic formulations of this compound may contain from 0.001 to 5% and especially 0.001 to 0.1% of medicament. Higher dosages as, for example, up to about 10% or lower dosages can be employed provided the dose is effective in reducing intraocular pressure, treating glaucoma, increasing blood flow velocity or oxygen tension. For a single dose, from between 0.001 to 5.0 mg, preferably 0.005 to 2.0 mg, and especially 0.005 to 1.0 mg of the compound can be applied to the human eye.

The pharmaceutical preparation which contains the compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, peanut oil, polyalkylene glycols, petroleum based jelly, ethyl cellulose, ethyl oleate, carboxymethyl-cellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a microparticle formulation. The pharmaceutical preparation may also be in the form of a solid insert. For example, one may use a solid water soluble polymer as the carrier for the medicament. The polymer used to form the insert may be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates such as polyacrylic acid salts, ethylacrylates, polyactylamides; natural products such as gelatin, alginates, pectins, tragacanth, karaya, chondrus, agar, acacia; the starch derivatives such as starch acetate, hydroxymethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, gellan gum, and mixtures of said polymer.

Suitable subjects for the administration of the formulation of the present invention include primates, man and other animals, particularly man and domesticated animals such as cats, rabbits and dogs.

The pharmaceutical preparation may contain non-toxic auxiliary substances such as antibacterial components which are non-injurious in use, for example, thimerosal, benzalkonium chloride, methyl and propyl paraben, benzyldodecinium bromide, benzyl alcohol, or phenylethanol; buffering ingredients such as sodium chloride, sodium borate, sodium acetate, sodium citrate, or gluconate buffers; and other conventional ingredients such as sorbitan monolaurate, triethanolamine, polyoxyethylene sorbitan monopalmitylate, ethylenediamine tetraacetic acid, and the like.

The ophthalmic solution or suspension may be administered as often as necessary to maintain an acceptable IOP level in the eye. It is contemplated that administration to the mammalian eye will be from once up to three times daily.

For topical ocular administration the novel formulations of this invention may take the form of solutions, gels, ointments, suspensions or solid inserts, formulated so that a unit dosage comprises a therapeutically effective amount of the active component or some multiple thereof in the case of a combination therapy.

The compounds of the instant invention are also useful for mediating the bone modeling and remodeling processes of the osteoblasts and osteoclasts. See PCT US99/23757 filed Oct. 12, 1999 and incorporated herein by reference in its entirety. The major prostaglandin receptor in bone is $EP_4$, which is believed to provide its effect by signaling via cyclic AMP. See Ikeda T, Miyaura C, Ichikawa A, Narumiya S, Yoshiki S and Suda T 1995, *In situ localization of three subtypes ($EP_1$, $EP_3$ and $EP_4$) of prostaglandin E receptors in embryonic and newborn mice., J Bone Miner Res* 10 (sup 1):S172, which is incorporated by reference herein in its entirety. Use of the compounds of formula I for the manufacture of a medicament for mediating the bone modeling and remodeling processes are also included in this invention Thus, another object of the present invention is to provide methods for stimulating bone formation, i.e. osteogenesis, in a mammal comprising administering to a mammal in need thereof a therapeutically effective amount of an $EP_4$ receptor subtype agonist of formula I.

Still another object of the present invention to provide methods for stimulating bone formation in a mammal in need thereof comprising administering to said mammal a therapeutically effective amount of an $EP_4$ receptor subtype agonist of formula I and a bisphosphonate active. Use of the compounds of formula I for the manufacture of a medicament for stimulating bone formation is also included in this invention.

Yet another object of the present invention to provide pharmaceutical compositions comprising a therapeutically effective amount of an $EP_4$ receptor subtype agonist of formula I and a bisphosphonate active.

It is another object of the present invention to provide methods for treating or reducing the risk of contracting a disease state or condition related to abnormal bone resorption in a mammal in need of such treatment or prevention, comprising administering to said mammal a therapeutically effective amount of an $EP_4$ receptor subtype agonist of formula I. Use of the compounds of formula I for the manufacture of a medicament for treating or reducing the risk of contracting a disease state or condition related to abnormal bone resorption is also included in this invention.

The disease states or conditions related to abnormal bone resorption include, but are not limited to, osteoporosis, glucocorticoid induced osteoporosis, Paget's disease, abnormally increased bone turnover, periodontal disease, tooth loss, bone fractures, rheumatoid arthritis, periprosthetic osteolysis, osteogenesis imperfecta, metastatic bone disease, hypercalcemia of malignancy, and multiple myeloma.

Within the method comprising administering a therapeutically effective amount of an $EP_4$ receptor subtype agonist of formula I and a bisphosphonate active, both concurrent and sequential administration of the $EP_4$ receptor subtype agonist of formula I and the bisphosphonate active are deemed within the scope of the present invention. Generally, the formulations are prepared containing 5 or 10 mg of a bisphosphonate active, on a bisphosphonic acid active basis. With sequential administration, the agonist and the bisphosphonate can be administered in either order. In a subclass of sequential administration the agonist and bisphosphonate are typically administered within the same 24 hour period. In yet a further subclass, the agonist and bisphosphonate are typically administered within about 4 hours of each other.

Nonlimiting examples of bisphosphonate actives useful herein include the following:

Alendronic acid, 4-amino-1-hydroxybutylidene-1,1-bisphosphonic acid;

Alendronate (also known as alendronate sodium or alendronate monosodium trihydrate), 4-amino-1-hydroxybutylidene-1,1-bisphosphonic acid monosodium trihydrate;

Alendronic acid and alendronate are described in U.S. Pat. No. 4,922,007, to Kieczykowski et al., issued May 1, 1990; U.S. Pat. No. 5,019,651, to Kieczykowski et al., issued May 28, 1991; U.S. Pat. No. 5,510,517, to Dauer et al., issued Apr. 23, 1996; U.S. Pat. No. 5,648,491, to Dauer et al., issued Jul. 15, 1997, all of which are incorporated by reference herein in their entirety;

Cycloheptylaminomethylene-1,1-bisphosphonic acid, YM 175, Yamanouchi (cimadronate), as described in U.S. Pat. No. 4,970,335, to Isomura et al., issued Nov. 13, 1990, which is incorporated by reference herein in its entirety;

1,1-dichloromethylene-1,1-diphosphonic acid (clodronic acid), and the disodium salt (clodronate, Procter and Gamble), are described in Belgium Patent 672,205 (1966) and *J. Org. Chem* 32, 4111 (1967), both of which are incorporated by reference herein in their entirety;

1-hydroxy-3-(1-pyrrolidinyl)-propylidene-1,1-bisphosphonic acid (EB-1053);

1-hydroxyethane-1,1-diphosphonic acid (etidronic acid);

1-hydroxy-3-(N-methyl-N-pentylamino)propylidene-1,1-bisphosphonic acid, also known as BM-210955, Boehringer-Mannheim (ibandronate), is described in U.S. Pat. No. 4,927,814, issued May 22, 1990, which is incorporated by reference herein in its entirety;

6-amino-1-hydroxyhexylidene-1,1-bisphosphonic acid (neridronate);

3-(dimethylamino)-1-hydroxypropylidene-1,1-bisphosphonic acid (olpadronate);

3-amino-1-hydroxypropylidene-1,1-bisphosphonic acid (pamidronate);

[2-(2-pyridinyl)ethylidene]-1,1-bisphosphonic acid (piridronate) is described in U.S. Pat. No. 4,761,406, which is incorporated by reference in its entirety;

1-hydroxy-2-(3-pyridinyl)-ethylidene-1,1-bisphosphonic acid (risedronate);

(4-chlorophenyl)thiomethane-1,1-disphosphonic acid (tiludronate) as described in U.S. Pat. No. 4,876,248, to Breliere et al., Oct. 24, 1989, which is incorporated by reference herein in its entirety; and 1-hydroxy-2-(1H-imidazol-1-yl)ethylidene-1,1-bisphosphonic acid (zolendronate).

A non-limiting class of bisphosphonate actives useful in the instant invention are selected from the group consisting of alendronate, cimadronate, clodronate, tiludronate, etidronate, ibandronate, neridronate, olpandronate, risedronate, piridronate, pamidronate, zolendronate, pharmaceutically acceptable salts thereof, and mixtures thereof.

A non-limiting subclass of the above-mentioned class in the instant case is selected from the group consisting of alendronate, pharmaceutically acceptable salts thereof, and mixtures thereof.

A non-limiting example of the subclass is alendronate monosodium trihydrate.

In the present invention, as it relates to bone stimulation, the agonist is typically administered for a sufficient period of time until the desired therapeutic effect is achieved. The term "until the desired therapeutic effect is achieved", as used herein, means that the therapeutic agent or agents are continuously administered, according to the dosing schedule chosen, up to the time that the clinical or medical effect sought for the disease or condition being mediated is observed by the clinician or researcher. For methods of treatment of the present invention, the compounds are continuously administered until the desired change in bone mass or structure is observed. In such instances, achieving an increase in bone mass or a replacement of abnormal bone structure with normal bone structure are the desired objectives. For methods of reducing the risk of a disease state or condition, the compounds are continuously administered for as long as necessary to prevent the undesired condition. In such instances, maintenance of bone mass density is often the objective.

Nonlimiting examples of administration periods can range from about 2 weeks to the remaining lifespan of the mammal. For humans, administration periods can range from about 2 weeks to the remaining lifespan of the human, preferably from about 2 weeks to about 20 years, more preferably from about 1 month to about 20 years, more preferably from about 6 months to about 10 years, and most preferably from about 1 year to about 10 years.

The instant compounds are also useful in combination with known agents useful for treating or preventing bone loss, bone fractures, osteoporosis, glucocorticoid induced osteoporosis, Paget's disease, abnormally increased bone turnover, periodontal disease, tooth loss, osteoarthritis, rheumatoid arthritis, periprosthetic osteolysis, osteogenesis imperfecta, metastatic bone disease, hypercalcemia of malignancy, and multiple myeloma. Combinations of the presently disclosed compounds with other agents useful in treating or preventing osteoporosis or other bone disorders are within the scope of the invention. A person of ordinary skill in the art would be able to discern which combinations of agents would be useful based on the particular characteristics of the drugs and the disease involved. Such agents include the following: an organic bisphosphonate; a cathepsin K inhibitor; an estrogen or an estrogen receptor modulator; an androgen receptor modulator; an inhibitor of osteoclast proton ATPase; an inhibitor of HMG-CoA reductase; an integrin receptor antagonist; an osteoblast anabolic agent, such as PTH; calcitonin; Vitamin D or a synthetic Vitamin D analogue; and the pharmaceutically acceptable salts and mixtures thereof. A preferred combination is a compound of the present invention and an organic bisphosphonate. Another preferred combination is a compound of the present invention and an estrogen receptor modulator. Another preferred combination is a compound of the present invention and an estrogen. Another preferred combination is a compound of the present invention and an androgen receptor modulator. Another preferred combination is a compound of the present invention and an osteoblast anabolic agent.

Regarding treatment of abnormal bone resorption and ocular disorders, the formula I agonists generally have an $EC_{50}$ value from about 0.001 nM to about 100 microM, although agonists with activities outside this range can be useful depending upon the dosage and route of administration. In a subclass of the present invention, the agonists have an $EC_{50}$ value of from about 0.01 microM to about 10 microM. In a further subclass of the present invention, the agonists have an $EC_{50}$ value of from about 0.1 microM to about 10 microM. $EC_{50}$ is a common measure of agonist activity well known to those of ordinary skill in the art and is defined as the concentration or dose of an agonist that is needed to produce half, i.e. 50%, of the maximal effect. See also, Goodman and Gilman's, *The Pharmacologic Basis of Therapeutics*, 9th edition, 1996, chapter 2, E. M. Ross, *Pharmacodynamics, Mechanisms of Drug Action and the Relationship Between Drug Concentration and Effect*, and PCT US99/23757, filed Oct. 12, 1999, which are incoroporated by reference herein in their entirety.

The herein examples illustrate but do not limit the claimed invention. Each of the claimed compounds are $EP_4$ agonists and are useful for a number of physiological ocular and bone disorders.

The compounds of this invention can be made, with some modification, in accordance with U.S. Pat. No. 6,043,275, $EP_{0855389}$, and WO 01/46140, all of which are incorporated herein by reference in their entirety. The following nonlimiting examples, given by way of illustration, is demonstrative of the present invention.

Compounds stated in the present invention can be prepared according to the following general scheme.

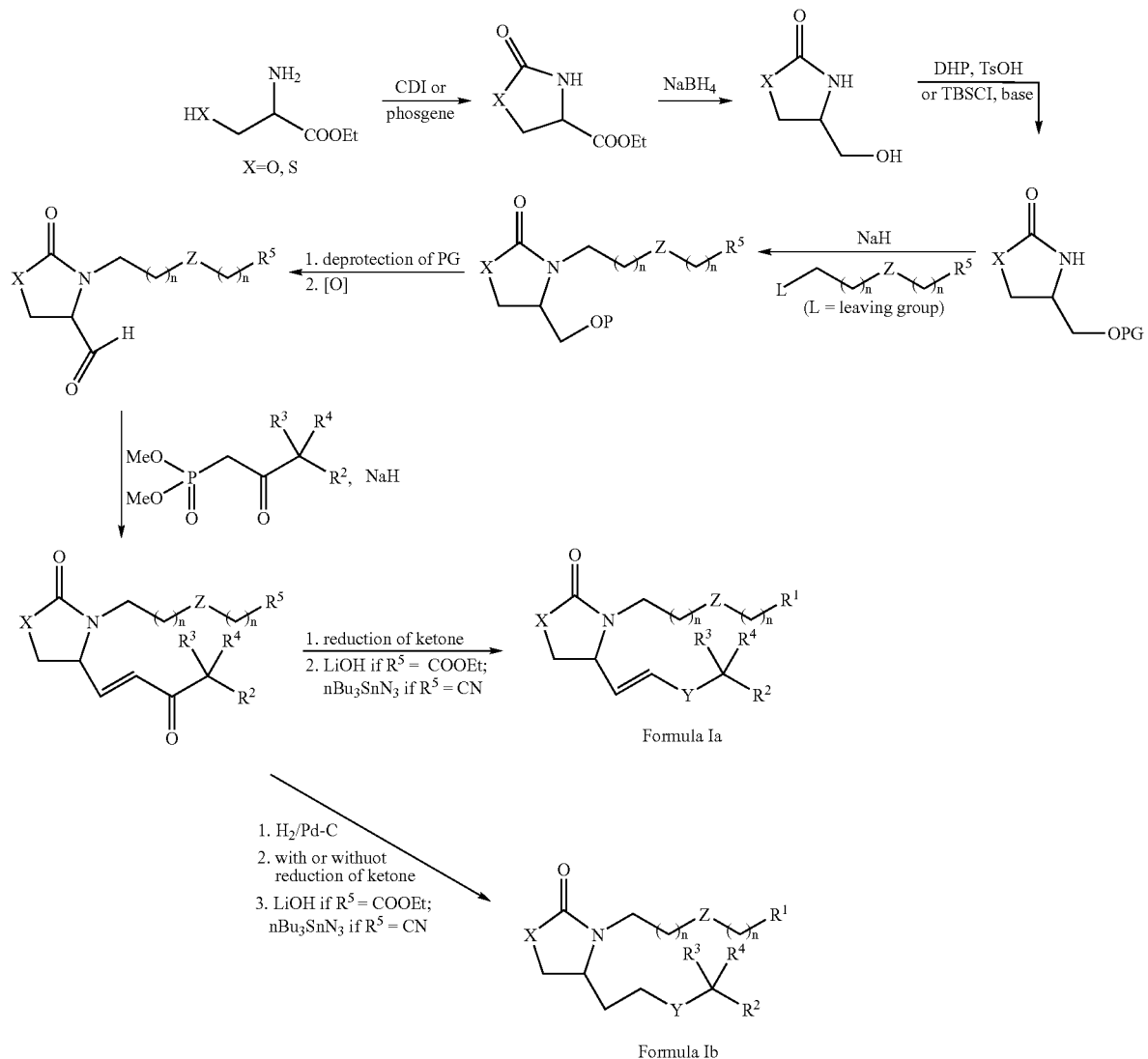

The variables are as defined in Formula I.

Some abbreviations that may appear in this application are as follows:

ABBREVIATIONS

| Designation | |
|---|---|
| CDI | 1,1'-carbonyldiimidazole |
| DHP | 4-dihydro-2H-pyran |
| LiOH | lithium hydroxide |
| NaBH4 | sodium borohydride |
| NaH | sodium hydride |
| nBu3SnN3 | azidotributyltin. |
| PG | protecting groups |
| TBSCl | tert-butyldimethylsilyl chloride |
| TsOH | p-toluenesulfonic acid |

Preparation of compounds in the present invention is further illustrated by the following specific examples.

EXAMPLE 1

7-{4-[(1E,3S)-3-hydroxy-4-phenylbut-1-enyl]-2-oxo-1,3-oxazolidin-3-yl}heptanoic acid (1-10) and 7-{4-[(1E,3R)-3-hydroxy-4-phenylbut-1-enyl]-2-oxo-1,3-oxazolidin-3-yl}heptanoic acid (1-11)

Step 1: 4-methoxycarbonyloxazolidin-2-one (1-1)

The preparation of 1-1 was carried out according to the literature procedure (see: Sibi, M. P. et al, *J. Chem. Soc. Perkin Trans.* 1 1994, 1675). Thus, 39.5 grams of serine methyl ester hydrochloride was reacted with phosgene (20% solution in toluene, 175 mL) to give 42 grams of desired product. $^1$H NMR (400 MHz, acetone-$d_6$): δ 7.1 (br s, 1H, NH), 4.64–4.56 (m, 2H), 4.44 (dd, 1H), 3.77 (s, 3H).

Step 2: N-Boc4-methoxycarbonyloxazolidin-2-one (1-2)

The preparation of this compound was carried out according to the method described by Ishizuka and Kunieda (see: *Tetrahedron Lett.* 1987, 28, 4185). Thus, to a solution of 1-1 (1 g, 6.9 mmol) in THF was added di-t-butyl dicarbonate (1.81 g), triethylamine (1.16 mL) and DMAP (84 mg). The solution was stirred at room temperature overnight and diluted with water/ethyl acetate. The organic layer was separated, washed with 1N HCl, half saturated NaHCO$_3$ and brine. The crude product thus obtained was used without further purification. $^1$H NMR (500 MHz, acetone-d$_6$): δ 4.92 (dd, 1H), 4.62 (t, 1H), 4.35 (dd, 1H), 3.80 (s, 3H), 1.46 (s, 9H).

Step 3: tert-Butyl(2-oxo-1,3-oxazolidin-4-yl)methyl carbonate (1-3)

To a solution of 1-2 (6.9 mmol) in ethanol/THF at 0° C. was added NaBH$_4$ (522 mg) and the mixture was allowed to warm slowly to room temperature and then quenched with saturated NH$_4$Cl and extracted with ethyl acetate. Purification by column chromatography (70%–100% ethyl acetate in hexanes) afforded compound 1-3 as a white solid. $^1$H NMR (400 MHz, acetone-d$_6$): δ 6.81 (br s, 1H, NH), 4.50 (t, 1H), 4.20 (m, 3H), 4.10 (dd, 1H), 1.46 (s, 9H); MS (+ESI): m/z 218.1 [M+1]$^+$.

Step 4: Ethyl 7-(4-{[(tert-butoxycarbonyl)oxy]methyl}-2-oxo-1,3-oxazolidin-3-yl)heptanoate (1-4)

To a solution of 1-3 (340 mg) and KI (240 mg) in DMF (16 mL) was added NaH (69 mg) and the mixture was stirred at room temperature for 1 h. To the mixture was then added ethyl 7-bromoheptanoate (247 mg) and the mixture was heated to 70° C. overnight. After cooling to room temperature, the mixture was diluted with ether/water and extracted with ether (3×). The organic layer was washed with water, brine and dried over Na$_2$SO$_4$. The crude was purified by flash chromatography. Eluting with 50% ethyl acetate in hexanes gave the desired product. $^1$H NMR (500 MHz, acetone-d$_6$): δ 4.43–4.34 (m, 2H), 4.19–4.11 (m, 3H), 4.09 (q, 2H), 3.40 (m, 1H), 3.17 (m, 1H), 2.30 (t, 2H), 1.70–1.50 (m, 4H), 1.47 (s, 9H), 1.40–1.30 (m, 4H), 1.22 (t, 3H).

Step 5: Ethyl 7-[4-(hydroxymethyl)-2-oxo-1,3-oxazolidin-3-yl]heptanoate (1-5)

A solution of 1-4 (446 mg) in a mixture of 10% TFA in dichloromethane (10 mL) was stirred at room temperature for 2 h and concentrated. The residue was purified by column chromatography. Eluting with 70–100% ethyl acetate in hexanes afforded the alcohol 1-5 (264 mg). $^1$H NMR (400 MHz, acetone-d$_6$): δ 4.33 (t, 1H), 4.19 (t, 1H, OH), 4.14 (dd, 1H), 4.09 (q, 2H), 3.95 (m, 1H), 3.78 (m, 1H), 3.65 (m, 1H), 3.38 (m, 1H), 3.16 (m, 1H), 2.29 (t, 2H), 1.70–1.55 (m, 4H), 1.45–1.30 (m, 4H), 1.21 (t, 3H).

Step 6: Ethyl 7-{4-[(1E)-3-oxo-4-phenylbut-1-enyl]-2-oxo-1,3-oxazolidin-3-yl}heptanoate (1-6)

To a solution of alcohol 1-5 (273 mg) in dichloromethane (5 mL) was added Dess-Martin periodinane (451 mg) and the mixture was stirred at room temperature for 1 h and concentrated. The mixture was resuspended in ether, filtered and the filtrate was washed with saturated NaHCO$_3$ and dried over Na$_2$SO$_4$. Filtration and concentration in vacuo afforded the crude aldehyde Ethyl 7-(4-formyl-2-oxo-1,3-oxazolidin-3-yl)heptanoate (1-7) which was used directly without further purification. To a suspension of NaH (47 mg) in THF (6 mL) was added dimethyl 2-oxo-3-phenylpropylphosphonate (282 mg) at 0° C. (formed a white slurry) and the mixture was stirred for an additional 1 h. To the mixture was then added aldehyde 1-7 (145 mg) in THF (4 mL) via cannula and the resultant mixture stirred at room temperature for 2 h and quenched with saturated NH$_4$Cl. The mixture was then extracted with ethyl acetate (3×) and the organic layer was washed with brine, dried over Na$_2$SO$_4$, filtered and concentrated. The residue was purified by chromatography using ethyl acetate/hexanes (1:1) as the eluent to give the desired product 1-6. $^1$H NMR (400 mg, acetone-d$_6$): δ 7.36–7.26 (m, 5H), 6.86 (dd, 1H), 6.43 (d, 1H), 4.57 (m, 1H), 4.50 (t, 1H), 4.12–3.96 (m, 5H), 3.28 (m, 1H), 2.96 (m, 1H), 2.28 (t, 2H), 1.65–1.45 (m, 4H), 1.35–1.25, m, 4H), 1.22 (t, 3H).

Step 7: Ethyl 7-{4-[(1E,3R)-3-hydroxy-4-phenylbut-1-enyl]-2-oxo-1,3-oxazolidin-3-yl}heptanoate (1-8) and Ethyl 7-{4-[(1E,3S)-3-hydroxy-4-phenylbut-1-enyl]-2-oxo-1,3-oxazolidin-3-yl}heptanoate (1-9)

To a solution of ketone 1-6 (128 mg) in methanol/AcOH (2.5:1, 3.5 mL) was added Na(CN)BH$_3$ (25 mg) and the mixture was stirred at room temperature for 2 h and then heated briefly with a heat gun. The mixture was then quenched with water and extracted with ethyl acetate (3×) and the organic layers was concentrated and purified by chromatography. Eluting with 50–75% ethyl acetate in hexanes first gave isomer 1-8. $^1$H NMR (400 MHz, acetone-d$_6$): δ 7.35–7.15 (m, 5H), 5.92 (dd, 1H), 5.50 (m, 1H), 4.45–4.30 (m, 3H), 4.18 (d, 1H), 4.08 (q, 2H), 3.75 (m, 1H), 3.22 (m, 1H), 3.00–2.80 (m, 3H), 2.29 (t, 2H), 1.65–1.45 (m, 4H), 1.40–1.30 (m, 4H), 1.21 (t, 3H). For convenience, the less polar isomer was arbitrarily assigned epimer 1-8. Continuous elution afforded the more polar epimer 1-9. $^1$H NMR (400 MHz, acetone-d$_6$): δ 7.35–7.15 (m, 5H), 5.91 (dd, 1H), 5.50 (m, 1H), 4.46–4.29 (m, 3H), 4.15 (d, 1H), 4.08 (q, 2H), 3.82 (dd, 1H), 3.15 (m, 1H), 2.95–2.75 (m, 3H), 2.29 (t, 2H), 1.65–1.25 (m, 8H), 1.22 (t, 3H).

A mixture of ester 1-9 (22 mg) in methanol (0.7 mL) and water (0.15 mL) and LiOH (0.062 mL, 1 N) was stirred at room temperature under N$_2$ overnight and concentrated to give the title compound 1-10 as a lithium salt. MS (−ESI): m/z 360.1 (M−1)$^-$. Epimer 1-8 was processed to the title compound 1-11 similarly. MS (−ESI): m/z 360.1 (M−1)$^-$.

EXAMPLE 2

(4S)-4-[(1E,3R)-4,4-difluoro-3-hydroxy-4-phenylbut-1-enyl]-3-[6-(1H-tetraazol-5-yl)hexyl]-1,3-oxazolidin-2-one (2-8) and (4S)-4-[(1E,3S)-4,4-difluoro-3-hydroxy-4-phenylbut-1-enyl]-3-[6-(1H-tetraazol-5-yl)hexyl]-1,3-oxazolidin-2-one (2-9)

Step 1: methyl N-(6-cyanohexyl)-D-serinate (2-1)

To a solution of D-serine methyl ester hydrochloride (0.91 g) in ethanol (18 mL) was added 7-oxoheptanenitrile (0.67 g) and triethylamine (0.6 mL) (see: Kubodera, N. et al, *Heterocycles* 1982, 19, 1285) and the mixture was stirred under N$_2$ for 1 h. To the solution was then added Na(CN)BH$_3$ (0.4 g) and the resultant cloudy suspension was further stirred under N$_2$ for 1 h. The mixture was quenched with water and concentrated in vacuo and the residue diluted with ethyl acetate/saturated NaHCO$_3$. The organic layer was separated and the aqueous layer extracted with ethyl acetate (3×). The organic layers were washed with water, brine, dried over Na$_2$SO$_4$ and filtered. The filtrate was concentrated and the residue was purified by chromatography. Eluting with 5–10% (v) methanol in dichloromethane gave the desired product 2-1 (620 mg). $^1$H NMR (400 MHz, CDCl$_3$): δ 3.78 (m, 1H), 3.77 (s, 3H), 3.59 (dd, 1H), 3.38 (dd, 1H), 2.72 (m, 1H), 2.53 (m, 1H), 2.36 (t, 2H), 1.70 (m, 2H), 1.55–1.35 (m, 6H).

Step 2: methyl(4R)-3-(6-cyanohexyl)-2-oxo-1,3-oxazolidine-4-carboxylate (2-2)

To a solution of amine 2-1 (620 mg) and pyridine (0.48 mL) in dichloromethane (10 mL) at 0° C. was added a solution of phosgene in toluene (1.72 mL, 1.9 M) and the mixture was stirred at the temperature for 1 h. The mixture was diluted with dichloromethane and washed with 1 N HCl and brine, and dried over $Na_2SO_4$. Filtration and concentration of the filtrate gave the crude product which was purified by chromatography. Eluting with 60% ethyl acetate in hexanes afforded the desired product 2-2 (560 mg). $^1$H NMR (400 MHz, acetone-$d_6$): δ 4.61 (dd, 1H), 4.52 (t, 1H), 4.35 (dd, 1H), 3.80 (s, 3H), 3.48 (m, 1H), 3.15 (m, 1H), 2.47 (t, 2H), 1.75–1.35 (m, 8H).

Step 3: 7-[(4S)-4-(hydroxymethyl)-2-oxo-1,3-oxazolidin-3-yl]heptanenitrile (2-3)

To a solution of ester 2-2 (560 mg) in ethanol (5 mL) at 0° C. was added $NaBH_4$ (38 mg) and the mixture was stirred at the temperature for 1 h and quenched with half saturated NaCl. The mixture was concentrated in vacuo to remove the ethanol and the residue was extracted with ethyl acetate (3×). The organic layers were washed with brine, dried over $Na_2SO_4$, filtered and concentrated in vacuo to afford the desired alcohol 2-3 (480 mg). $^1$H NMR (400 MHz, acetone-$d_6$): δ 4.33 (t, 1H), 4.20–4.12 (m, 2H), 3.96 (m, 1H), 3.79 (m, 1H), 3.65 (m, 1H), 3.40 (m, 1H), 3.17 (m, 1H), 2.47 (t, 2H), 1.70–1.35 (m, 8H).

Step 4: 7-{(4S)-4-[(1E)-4,4-difluoro-3-oxo-4-phenylbut-1-enyl]-2-oxo-1,3-oxazolidin-3-yl}heptanenitrile (2-4)

To a solution of alcohol 2-3 (480 mg) in dichloromethane (10 mL) was added Dess-Martin periodanane (1 g) and the mixture was stirred at room temperature for 1 h and concentrated. The residue was co-evaporated with toluene several times, resuspended in ethyl acetate and was allowed to sit at 5° C. overnight. The mixture was filtered and the filtrate was concentrated to give the crude aldehyde 7-[(4S)$_4$-formyl-2-oxo-1,3-oxazolidin-3-yl]heptanenitrile (2-5) which was used directly. To a suspension of NaH (168 mg) in THF was added dimethyl 3,3-difluoro-2-oxo-3-phenylpropylphosphonate (1.1 g) dropwise at 0° C. and the mixture was stirred at the temperature for 30 min. To the mixture was added crude aldehyde 2-5 in THF via a cannula and the mixture was stirred at room temperature for 5 h and quenched with saturated $NH_4Cl$. The mixture was extracted with ethyl acetate and the organic layer was dried and concentrated. The residue was purified by flash chromatography to give the desired product 2-4. $^1$H NMR (400 MHz, acetone-$d_6$): δ 7.70–7.55 (m, 5H), 7.08 (dd, 1H), 6.95 (d, 1H), 4.70 (m, 1H), 4.52 (t, 1H), 3.30 (m, 1H), 3.00 (m, 1H), 2.48 (t, 2H), 1.70–1.25 (m, 8H).

Step 5: 7-{(4S)-4-[(1E,3R)-4,4-difluoro-3-hydroxy-4-phenylbut-1-enyl]-2-oxo-1,3-oxazolidin-3-yl}heptanenitrile (2-6) and 7-{(4S)-4-[(1E,3S)-4,4-difluoro-3-hydroxy-4 phenylbut-1-enyl]-2-oxo-1,3-oxazolidin-3-yl}heptanenitrile (2-7)

To a solution of ketone 2-4 (100 mg) and $CeCl_3 \cdot 7H_2O$ (1 eq) in ethanol/water (4:1) at −20° C. was added $NaBH_4$ (1.2 eq) and the mixture was warmed slowly to room temperature and quenched with half saturated NaCl. The mixture was processed as described and the crude was purified by HPLC (porasil™). Eluting with 60% ethyl acetate in hexanes first afforded epimer 2-7 in which the OH group was arbitrarily assigned the β-orientation for convenience. $^1$H NMR (400 MHz, acetone-$d_6$): δ 7.57–7.48 (m, 5H), 5.96 (dd, 1H), 5.77 (m, 1H), 5.20 (d, 1H), 4.70 (m, 1H), 4.45–4.35 (m, 2H), 3.81 (m, 1H), 3.18 (m, 1H), 2.85 (m, 1H), 2.47 (t, 2H), 1.68 (m, 2H), 1.55–1.25 (m, 6H).

Continuous elution gave isomer 2-6. $^1$H NMR (400 MHz, acetone-$d_6$): δ 7.57–7.48 (m, 5H), 5.93 (dd, 1H), 5.77 (m, 1H), 5.12 (d, 1H), 4.70 (m, 1H), 4.45–4.35 (m, 2H), 3.81 (m, 1H), 3.20 (m, 1H), 2.87 (m, 1H), 2.47 (t, 2H), 1.68 (m, 2H), 1.55–1.25 (m, 6H).

Step 6:

A solution of nitrile 2-6 (24 mg) in toluene (1 mL) and tributyltin azide (0.2 m) was heated to 120° C. for 5 h and cooled to room temperature. The mixture was diluted with ethyl acetate and stirred vigorously with a 5% aqueous solution of KF for 1 h. The mixture was filtered and the filtrate was extracted with ethyl acetate. The ethyl acetate layer was washed with brine, dried over $Na_2SO_4$, filtered and concentrated. The residue was purified by column chromatography. Eluting with 0–10% methanol in dichloromethane gave the title compound 2-8. MS (−ESI): m/z 420.3 (M−1)$^-$. Compound 2-9 was prepared from the less polar nitrile 2-7 similarly. MS (−ESI): m/z 420.3 (M−1)$^-$.

EXAMPLE 3

7-{(4S)-4-[(1E)-3-hydroxy-4-phenylbut-1-enyl]-2-oxo-1,3-thiazolidin-3-yl}heptanoic acid (3-9)

Step 1: ethyl D-cysteinate (3-1):

To a solution of D-cysteine (12 g) in 200 mL anhydrous ethanol was bubbled in anhydrous hydrogen chloride for 15 minutes. The solution was allowed to stir at room temperature overnight afterwhich it was concentrated in vacuo to yield 13 g (93%) of 3-1 as a white solid whose $^1$H NMR data was identical to that reported in the literature.

Step 2: ethyl(4R)-2-oxo-1,3-thiazolidine-4-carboxylate (3-2):

To a solution of 3-1 (8.5 g, 22.6 mmol) in 200 mL THF was added of carbonyl diimidazole (12.5 g) and the solution was stirred overnight at room temperature. The solution was concentrated in vacuo, 200 mL of 5% $Na_2CO_3$ was added and the solution stirred for one hour whereupon 6M HCl was added until the pH of the solution remained at 2. The solution was extracted with EtOAc, the organic phases were then combined, dried over $MgSO_4$, filtered and concentrated in vacuo. The compound was purified by flash chromatography using 40% EtOAc/hexanes to yield 6.7 g of 3-2 as a colorless oil. $^1$H NMR (400 MHz, acetone-$d_6$): δ 7.5 (br s, 1H), 4.5 (dd, 1H), 4.2 (q, 2H), 3.8 (dd, 1H), 3.6 (dd, 1H), 1.2 (t, 3H).

Step 3: (4S)-4-(hydroxymethyl)-1,3-thiazolidin-2-one (3-3):

To a solution of 3-2 (6.8 g, 38.6 mmol) in 100 mL ethanol was added sodium borohydride (3.8 g, 100 mmol) at 0° C. The solution was stirred for 2 hours as it warmed to rt. The solution was slowly poured into saturated aqueous ammonium chloride solution and the solution was extracted with ethyl acetate (5×). The organic phases were then combined, dried over $MgSO_4$, filtered and concentrated in vacuo. The compound was purified by flash chromatography using 0–10% methanol/ethyl acetate to yield 3.3 g of 3-3 as a colorless oil. $^1$H NMR (400 MHz, acetone-$d_6$): ° 7.0 (br s, 1H), 4.2 (t, 1H), 4.0 (m, 1H), 3.6 (m, 2H), 3.5 (dd, 1H), 3.3 (dd, 1H).

Step 4: (4S)-4-[(tetrahydro-2H-pyran-2-yloxy)methyl]-1,3-thiazolidin-2-one (3-4):

To a solution of 3-3 (3.3 g, 25 mmol) and 20 mg of p-toluenesulfonic acid in $CH_2Cl_2$ (100 mL) was added 3,4-dihydro-2H-pyran (2.7 mL, 30 mmol) and the resulting solution was stirred at rt for 30 minutes. Triethylamine (0.1 mL) was added and the solution was concentrated in vacuo.

The compound was purified by flash chromatography using 40% EtOAc/hexanes to yield 4 g of 3-4 as a colorless oil. $^1$H NMR (400 MHz, acetone-$d_6$): δ 7.0 (br s, 1H), 4.6 (s, 1H), 4.0 (m, 1H), 3.8 (m, 2H), 3.6 (m, 3H), 3.3 (dd, 1H), 1.9–1.4 (m, 6H).

Step 5: ethyl 7-{(4S)-2-oxo-4-[(tetrahydro-2H-pyran-2-yloxy)methyl]-1,3-thiazolidin-3-yl}heptanoate (3-5):

To a solution of 3-4 (0.5 g, 2.3 mmol) in 10 mL DMF was added 60% sodium hydride (100 mg, 2.5 mmol) and the resulting solution was stirred for 1 hour whereupon ethyl-7-bromohepatanoate (1.2 g, 5 mmol) was added. The solution was heated to 70° C. and stirred overnight. The solution was then cooled to room temperature, slowly poured into saturated aqueous ammonium chloride solution and was extracted with 9:1 hexanes: $CH_2Cl_2$. The organic phases were then combined, dried over $MgSO_4$, filtered and concentrated in vacuo. The compound was purified by flash chromatography using 20–50% ethyl acetate/hexanes to yield 500 mg of 3-5 as a colorless oil. $^1$H NMR (400 MHz, acetone-$d_6$): δ 4.7 (s, 1H), 4.1 (m, 3H), 3.8 (m, 2H), 3.5 (m, 4H), 3.2 (m, 2H), 2.3 (m, 2H), 1.9–1.3 (m, 14H), 1.2 (m, 3H).

Step 6: ethyl 7-[(4S)-4-(hydroxymethyl)-2-oxo-1,3-thiazolidin-3-yl]heptanoate (3-6):

To a solution of 3-5 (0.5 g, 2.3 mmol) in 10 mL EtOH was added p-toluene sulfonic acid (50 mg) and the resulting solution was stirred overnight at room temperature Triethylamine (0.1 mL) was added and the solution was concentrated in vacuo. The compound was purified by flash chromatography using 80% EtOAc/hexanes to yield 0.4 g of 3-6 as a colorless oil. $^1$H NMR (400 MHz, acetone-$d_6$): □ 4.2 (t, 1H), 4.1 (q, 3H), 3.9 (m, 1H), 3.7 (m, 2H), 3.6 (m, 1H), 3.4 (dd, 1H), 3.3 (dd, 1H), 3.1 (m, 1H), 2.3 (t, 2H), 1.3–1.7 (m, 8H), 1.2 (t, 2H).

Step 7: ethyl 7-{(4S)-2-oxo-4-[(1E)-3-oxo-4-phenylbut-1-enyl]-1,3-thiazolidin-3-yl}heptanoate (3-7):

To a solution of 3-6 (0.56 g, 2.0 mmol) in 10 mL $CH_2Cl_2$ was added Dess Martin periodinane (0.98 g, 2.3 mmol) in portions and the resulting solution was stirred for 2 hours. The solution was concentrated in vacuo, to which toluene was added and concentrated thrice to remove acetic acid. The concentrate was then filtered through celite with $CH_2Cl_2$ and concentrated in vacuo. The crude product was then diluted in 5 mL of THF and added to a solution of the Wittig reagent dimethyl 2-oxo-3-phenylpropylphosphonate (0.75 g, 3.1 mmol) and 60% sodium hydride (0.12 g, 2.9 mmol) in 5 mL of THF at 0° C. which was premixed for half an hour. The reaction mixture was stirred for 15 minutes at the initial temperature and was allowed to warm up to room temperature for one hour and was stored at 4° C. overnight. The reaction was then quenched with saturated aqueous ammonium chloride solution and was extracted with ethyl acetate. The organic phases were then combined, sequentially washed with $H_2O$, brine and dried over $Na_2SO_4$. After filtration and concentration in vacuo, the compound was purified by flash chromatography using 50% ethyl acetate/hexanes to yield 400 mg of 3-7 as a colorless oil. $^1$H NMR (400 MHz, $CDCl_3$): δ 7.40–7.21 (m, 5H), 6.75 (dd, 1H), 6.31 (d, 1H), 4.14 (q, 2H), 3.89 (s, 2H), 3.57–3.45 (m, 3H), 3.01 (dd, 1H), 2.75 (m, 1H), 2.31 (t, 2H), 1.64–1.22 (m, 8H), 1.28 (t, 3H); MS (+ESI): m/z 404.2 (M+1)$^+$.

Step 8: ethyl 7-{(4S)-4-[(1E)-3-hydroxy-4-phenylbut-1-enyl]-2-oxo-1,3-thiazolidin-3-yl}heptanoate (3-8):

To a solution of 3-7 (0.4 g, 1.0 mmol) in 12 mL 5:1 MeOH:acetic acid was added sodium cyanoborohydride (100 mg, 1.4 mmol) and the resulting solution was stirred overnight at room temperature. The solution was quenched with water and was concentrated in vacuo. The concentrate was extracted with ethyl acetate and washed with 2M $Na_2CO_3$ and then brine, after which it was dried over $Na_2SO_4$, filtered and concentrated in vacuo. The compound was purified by flash chromatography using 60% ethyl acetate/hexanes to yield 400 mg of 3-8 as a colorless oil. Data shown is for the major diastereomer. $^1$H NMR (400 MHz, $CDCl_3$): δ 7.35–7.21 (m, 5H), 5.84 (dd, 1H), 5.66 (dd, 1H), 4.46 (q, 1H), 4.23 (q, 1H), 4.14 (q, 2H), 3.68–3.37 (m, 2H), 2.97 (dd, 1H), 2.88 (m, 2H), 2.78 (m, 1H), 2.30 (t, 2H), 1.64–1.30 (m, 8H), 1.27 (t, 3H); MS (+ESI): m/z 406.2 (M+1)$^+$.

Step 9: 7-{(4S)-4-[(1E)-3-hydroxy-4-phenylbut-1-enyl]-2-oxo-1,3-thiazolidin-3-yl}heptanoic acid (3-9):

To a solution of 3-8 (45 mg, 0.11 mmol) in 5.5 mL 2:2:1 THF:MeOH:water, at 0° C., was added lithium hydroxide (170 μL of a 2M solution in water) and the resulting solution was allowed to warm up to room temperature and stirred overnight. To the solution was added a 1M aqueous solution of HCl (1 mL) and the solution was extracted with ethyl acetate. The organic phases were then combined, washed with brine, dried over $MgSO_4$, filtered and concentrated in vacuo. The compound was purified by flash chromatography using 50–100% ethyl acetate/hexanes to yield 37 mg of 3-9 as a white solid. $^1$H NMR (400 MHz, $CD_3OD$): δ 7.30–7.18 (m, 5H), 5.81 (dd, 1H), 5.53 (dd, 1H), 4.39 (q, 1H), 4.33 (q, 1H), 3.45 (dd, 1H), 3.33 (m, 1H), 2.97 (m, 2H), 2.77 (dd, 1H), 2.67 (m, 1H), 2.30 (t, 2H), 1.65–1.21 (m, 8H); MS (+ESI): m/z 378.2 (M+1)$^+$.

EXAMPLE 4

(4S)-4-[(1E)-3-hydroxy-4-phenylbut-1-enyl]-3-[6-(1H-tetraazol-5-yl)hexyl]-1,3-thiazolidin-2-one (4-5)

Step 1: 7-{(4S)-2-oxo-4-[(tetrahydro-2H-pyran-2-yloxy)methyl]-1,3-thiazolidin-3-yl}heptanenitrile (4-1):

To a solution of 3-4 (0.73 g, 3.4 mmol) in 10 mL DMF was added 60% sodium hydride (140 mg, 3.5 mmol) and the resulting solution was stirred for 1 hour at 50° C. whereupon 7-bromoheptanonitrile (1.1 mL, 6.8 mmol) and tetrabutylammonium iodide (50 mg) were added. The solution was stirred at 50° C. overnight afterwhich it was cooled to room temperature, slowly poured into saturated aqueous ammonium chloride solution and was extracted with ether. The organic phases were then combined and sequentially washed with $H_2O$, brine and dried over $Na_2SO_4$, filtered and concentrated in vacuo. The compound was purified by flash chromatography using 40–50% ethyl acetate/hexanes to yield 970 mg of 4-1 as a colorless oil. $^1$H NMR (400 MHz, $CDCl_3$): δ 4.63 (m, 1H), 4.04–3.68 (m, 3H), 3.68–3.58 (m, 1H), 3.55 (m, 2H), 3.42 (dd, 1H), 3.22–3.04 (m, 2H), 2.36 (t, 2H), 1.86–1.44 (m, 12H), 1.38–1.30(m, 2H); MS (+ESI): m/z 327.2 (M+1)$^+$.

Step 2: 7-[(4S)-4-(hydroxymethyl)-2-oxo-1,3-thiazolidin-3-yl]heptanenitrile (4-2):

To a solution of 4-1 (0.97 g, 3.0 mmol) in 10 mL EtOH was added p-toluene sulfonic acid (50 mg) and the resulting solution was stirred overnight at room temperature. Triethylamine (0.1 mL) was added and the solution was concentrated in vacuo. The compound was purified by flash chromatography using 50–80% EtOAc/hexanes to yield 0.65 g of 4-2 as a colorless oil. $^1$H NMR (400 MHz, $CDCl_3$): δ

3.92–3.73 (m, 3H), 3.68–3.60 (m, 1H), 3.42 (dd, 1H), 3.28 (dd, 1H), 3.10 (m, 1H), 2.37(t, 2H), 1.71–1.46 (m, 6H), 1.39–1.33 (m, 2H); MS (+ESI): m/z 243.1 (M+1)$^+$.

Step 3: 7-{(4S)-2-oxo-4-[(1E)-3-oxo-4-phenylbut-1-enyl]-1,3-thiazolidin-3-yl}heptanenitrile (4-3):

To a solution of 4-2 (0.65 g, 2.7 mmol) in 15 mL CH$_2$Cl$_2$ was added Dess Martin periodinane (1.4 g, 3.2 mmol) portion wise and the resulting solution was stirred for 2 hours. The solution was concentrated in vacuo, to which toluene was added and concentrated thrice to remove acetic acid. The concentrate was then filtered through celite with CH$_2$Cl$_2$ and concentrated in vacuo. The crude product was then diluted in 7 mL of THF and added to a solution of the Wittig reagent dimethyl 2-oxo-3-phenylpropylphosphonate (1.3 g, 5.3 mmol) and 60% sodium hydride (0.2 g, 5.1 mmol) in 7 mL of THF at 0° C. which had been premixed 30 minutes. The reaction mixture was stirred for 15 minutes at the initial temperature and was allowed to warm up to room temperature for 1 hour. The solution was stored at 4° C. overnight, quenched with saturated aqueous ammonium chloride solution and was extracted with ethyl acetate. The organic phases were then combined, and sequentially washed with H$_2$O, brine and dried over Na$_2$SO$_4$, filtered and concentrated in vacuo. The compound was purified by flash chromatography using 40% ethyl acetate/hexanes to yield 350 mg of 4-3 as a colorless oil. $^1$H NMR (400 MHz, CDCl$_3$): δ 7.37–7.20 (m, 5H), 6.74 (dd, 1H), 6.31 (d, 1H), 4.34 (q, 1H), 3.88 (s, 2H), 3.54–3.44 (m, 2H), 3.01 (dd, 1H), 2.77 (m, 1H), 2.33 (t, 2H), 1.67–1.60 (m, 2H), 1.47–1.30 (m, 4H), 1.28–1.23 (m, 2H); MS (+ESI): m/z 356.9 (M+1)$^+$.

Step 4: 7-{(4S)-4-[(1E)-3-hydroxy-4-phenylbut-1-enyl]-2-oxo-1,3-thiazolidin-3-yl}heptanenitrile (4-4):

To a solution of 4-3 (0.15 g, 0.4 mmol) in 8 mL CH$_2$Cl$_2$ was added 1M (R)-CBS in toluene (0.45 mL, 0.45 mmol) and cooled to −40° C. to which a solution of catechol borane (0.13 mL, 1.2 mmol) in CH$_2$Cl$_2$ (1 mL) was added dropwise. The solution was stirred at −40° C. for one hour and allowed to warm up to −20° C. during the following two hours. The reaction mixture was quenched at −20° C. with 1 N HCl and was stirred for 4 hours at room temperature. The phases were separated and the organic phase was sequentially washed with 1N HCl, H$_2$O, 1 N NaOH, brine and dried over Na$_2$SO$_4$, filtered and concentrated in vacuo. The compound was purified by flash chromatography using 40–50% ethyl acetate/hexanes to yield 125 mg of 4-4 as a colorless oil. $^1$H NMR (400 MHz, CDCl$_3$): δ 7.37–7.21 (m, 5H), 5.84 (dd, 1H), 5.65 (dd, 1H), 4.46 (q, 1H), 4.22 (q, 1H), 3.86–3.35 (m, 2H), 2.97 (dd, 1H), 2.88 (m, 2H), 2.80 (m, 1H), 2.36 (t, 2H), 1.70–1.27 (m, 8H); MS (+ESI): m/z 359.0 (M+1)$^+$.

Step 5: (4S)-4-[(1E)-3-hydroxy-4-phenylbut-1-enyl]-3-[6-(1H-tetrazol-5-yl)hexyl]-1,3-thiazolidin-2-one (4-5):

To a solution of 4-4 (70 mg, 0.2 mmol) in 0.2 mL toluene was added tributyltin azide (0.27 mL, 1.0 mmol) and the resulting solution was stirred at reflux for 4 hours. Ethyl acetate (100 mL) was added and the solution was quenched with 5% aqueous KF (30 mL) and 1N HCl (30 mL). The layers were separated and the organic layer was washed with brine, dried over Na$_2$SO$_4$, filtered and concentrated in vacuo. The compound was purified by flash chromatography using 0–5% MeOH/CH$_2$Cl$_2$ to yield 50 mg of 4-5 as a colorless oil. $^1$H NMR (400 MHz, CD$_3$OD): δ7.29–7.17 (m, 5H), 5.81 (dd, 1H), 5.53 (dd, 1H), 4.38 (q, 1H), 4.33 (q, 1H), 3.45 (dd, 1H), 3.33 (m, 1H), 2.97 (m, 4H), 2.78 (m, 1H), 2.68 (m, 1H), 1.83–1.21 (m, 8H); MS (−ESI): m/z 400.2 (M−1)$^−$.

I. Effects of an EP$_4$ Agonist on Intraocular Pressure (IOP) in Rabbits and Monkeys.

Animals

Drug-naïve, male Dutch Belted rabbits and female cynomolgus monkeys are used in this study. Animal care and treatment in this investigation are in compliance with guidelines by the National Institute of Health (NIH) and the Association for Research in Vision and Ophthalmology (ARVO) resolution in the use of animals for research. All experimental procedures str approved by the Institutional Animal Care and Use Committee of Merck and Company.

Drug Preparation and Administration

Drug concentrations are expressed in terms of the active ingredient (base). The compounds of this invention are dissolved in physiological saline at 0.01, 0.001, 0.0001% for rabbit study and 0.05, 0.005% for monkey studies. Drug or vehicle aliquots (25 ul) are administered topically unilaterally or bilaterally. In unilateral applications, the contralateral eyes receive an equal volume of saline. Proparacaine (0.5%) is applied to the cornea prior to tonometry to minimize discomfort. Intraocular pressure (IOP) is recorded using a pneumatic tonometer (Alcon Applanation Pneumatonograph) or equivalent.

Statistical Analysis

The results are expressed as the changes in IOP from the basal level measured just prior to administration of drug or vehicle and represent the mean, plus or minus standard deviation. Statistical comparisons are made using the Student's t-test for non-paired data between responses of drug-treated and vehicle-treated animals and for paired data between ipsilateral and contralateral eyes at comparable time intervals. The significance of the date is also determined as the difference from the "t−0" value using Dunnett's "t" test. Asterisks represent a significance level of $p<0.05$.

A. Intraocular Pressure Measurement in Rabbits

Male Dutch Belted rabbits weighing 2.5–4.0 kg are maintained on a 12-hour light/dark cycle and rabbit chow. All experiments are performed at the same time of day to minimize variability related to diurnal rhythm. IOP is measured before treatment then the compounds of this invention or vehicle are instilled (one drop of 25 ul) into one or both eyes and IOP is measured at 30, 60, 120, 180, 240, 300, and 360 minutes after instillation. In some cases, equal number of animals treated bilaterally with vehicle only are evaluated and compared to drug treated animals as parallel controls.

B. Intraocular Pressure Measurements in Monkeys.

Unilateral ocular hypertension of the right eye is induced in female cynomolgus monkeys weighing between 2 and 3 kg by photocoagulation of the trabecular meshwork with an argon laser system (Coherent NOVUS 2000, Palo Alto, USA) using the method of Lee at al. (1985). The prolonged increase in intraocular pressure (IOP) results in changes to the optic nerve head that are similar to those found in glaucoma patients.

For IOP measurements, the monkeys are kept in a sitting position in restraint chairs for the duration of the experiment. Animals are lightly anesthetized by the intramuscular injection of ketamine hydrochloride (3–5 mg/kg) approximately five minutes before each IOP measurement and one drop of 0.5% proparacaine was instilled prior to recording IOP. IOP is measured using a pneumatic tonometer (Alcon Applanation Tonometer) or a Digilab pneumatonometer (Bio-Rad Ophthalmic Division, Cambridge, Mass., USA).

IOP is measured before treatment and generally at 30, 60, 124, 180, 300, and 360 minutes after treatment. Baseline values are also obtained at these time points generally two or three days prior to treatment. Treatment consists of instilling one drop of 25 ul of the compounds of this invention (0.05 and 0.005%) or vehicle (saline). At least one-week washout period is employed before testing on the same animal. The normotensive (contralateral to the hypertensive) eye is treated in an exactly similar manner to the hypertensive eye. IOP measurements for both eyes are compared to the corresponding baseline values at the same time point. Results are expressed as mean plus-or-minus standard deviation in mm Hg. The activity range of the compounds of this invention for ocular use is between 0.01 and 100,000 nM II. Radioligand binding assays:

The assays used to test these compounds were performed essentially as described in: Abramovitz M, Adam M, Boie Y, Carriere M, Denis D, Godbout C, Lamontagne S, Rochette C, Sawyer N, Tremblay N M, Belley M, Gallant M, Dufresne C, Gareau Y, Ruel R, Juteau H, Labelle M, Ouimet N, Metters K M. The utilization of recombinant prostanoid receptors to determine the affinities and selectivities of prostaglandins and related analogs. Biochim Biophys Acta 2000 Jan. 17;1483(2):285–293 and discussed below:

Stable Expression of Prostanoid Receptors in the Human Embryonic Kidney (HEK) 293(EBNA) Cell Line Prostanoid receptor (PG) cDNAs corresponding to full length coding sequences were subcloned into the appropriate sites of the mammalian expression vector pCEP4 (Invitrogen) pCEP4PG plasmid DNA was prepared using the Qiagen plasmid preparation kit (QIAGEN) and transfected into HEK 293(EBNA) cells using LipofectAMINE@ (GIBCO-BRL) according to the manufacturers' instructions. HEK 293(EBNA) cells expressing the cDNA together with the hygromycin resistance gene were selected in Dulbecco's Modified Eagle Medium (DMEM) supplemented with 10% heat inactivated fetal bovine serum, 1 mM sodium pyruvate, 100 U/ml Penicillin-G, 100 µg/ml Streptomycin sulphate, 250 µg/ml active GENETICIN™ (G418) (all from Life Technologies, Inc./BRL) and 200 µg/ml hygromycin (Calbiochem). Individual colonies were isolated after 2–3 weeks of growth under selection using the cloning ring method and subsequently expanded into clonal cell lines. Expression of the receptor cDNA was assessed by receptor binding assays.

HEK 293(EBNA) cells were grown in supplemented DMEM complete medium at 37° C. in a humidified atmosphere of 6% $CO_2$ in air, then harvested and membranes prepared by differential centrifugation (1000×g for 10 min, then 160,000×g for 30 min, all at 4° C.) following lysis of the cells by nitrogen cavitation at 800 psi for 30 min on ice in the presence of protease inhibitors (2 mM phenylmethylsulfonylfluoride, 10 µM E-64, 100 µM leupeptin and 0.05 mg/ml pepstatin). The 160,000×g pellets were resuspended in 10 mM HEPES/KOH (pH 7.4) containing 1 mM EDTA at approximately 5–10 mg/ml protein by Dounce homogenisation (Dounce A; 10 strokes), frozen in liquid nitrogen and stored at −80° C.

Prostanoid Receptor Binding Assays

Prostanoid receptor binding assays were performed in a final incubation volume of 0.2 ml in 10 mM MES/KOH (pH 6.0) (EP subtypes, FP and TP) or 10 mM HEPES/KOH (pH 7.4) (DP and IP), containing 1 mM EDTA, 10 mM $MgCl_2$ (EP subtypes) or 10 mM $MnCl_2$ (DP, FP, IP and TP) and radioligand [0.5–1.0 nM [$^3$H]$PGE_2$ (181 Ci/mmol) for EP subtypes, 0.7 nM [$^3$H]$PGD_2$ (115 Ci/mmol) for DP, 0.95 nM [$^3$H]$PGF_{2\alpha}$ (170 Ci/mmol) for FP, 5 nM [$^3$H]iloprost (16 Ci/mmol) for IP and 1.8 nM [$^3$H]SQ 29548 (46 Ci/mmol) for TP]. $EP_3$ assays also contained 100 µM GTPγS. The reaction was initiated by addition of membrane protein (approximately 30 µg for $EP_1$, 20 µg for $EP_2$, 2 µg for $EP_3$, 10 µg for $EP_4$, 60 µg for FP, 30 µg for DP, 10 µg for IP and 10 µg for TP) from the 160,000×g fraction. Ligands were added in dimethylsulfoxide ($Me_2SO$) which was kept constant at 1% (v/v) in all incubations. Non-specific binding was determined in the presence of 1 µM of the corresponding non-radioactive prostanoid. Incubations were conducted for 60 min (EP subtypes, PP and IP) or 30 min (DP and TP) at 30° C. (EP subtypes, DP, PP and TP) or room temperature (IP) and terminated by rapid filtration through a 96-well Unifilter GF/C (Canberra Packard) prewetted in assay incubation buffer without EDTA (at 4° C.) and using a Tomtec Mach III 96-well semi-automated cell harvester. The filters were washed with 3–4 ml of the same buffer, dried for 90 min at 55° C. and the residual radioactivity bound to the individual filters determined by scintillation counting with addition of 50 µl of Ultima Gold F (Canberra Packard) using a 1450 MicroBeta (Wallac). Specific binding was calculated by subtracting non-specific binding from total binding. Specific binding represented 90–95% of the total binding and was linear with respect to the concentrations of radioligand and protein used. Total binding represented 5–10% of the radioligand added to the incubation media.

The activity range of the compounds of this invention for bone use is between 0.01 and 100,000 nM.

Bone Resorption Assays:

1. Animal Procedures:

For mRNA localization experiments, 5-week old Sprague-Dawley rats (Charles River) are euthanized by $CO_2$, their tibiae and calvariae are excised, cleaned of soft tissues and frozen immediately in liquid nitrogen. For $EP_4$ regulation experiments, 6-week old rats are given a single injection of either vehicle (7% ethanol in sterile water) or an anabolic dose of $PGE_2$ (Cayman Chemical, Ann Arbor, Mich.), 3–6 mg/kg in the same vehicle) intraperitoneally. Animals are euthanized at several time points post-injection and their tibiae and calvariae, as well as samples from lung and kidney tissues are frozen in liquid nitrogen.

2. Cell Cultures

RP-1 periosteal cells are spontaneously immortalized from primary cultures of periosteal cells from tibae of 4-week old Sprague-Dawley rats and are cultured in DMEM (BRL, Gaithersburg, Md.) with 10% fetal bovine serum (JRH Biosciences, Lenexa, Kans.). These cells do not express osteoblastic phenotypic markers in early culture, but upon confluence, express type I collagen, alkaline phosphatase and osteocalcin and produce mineralized extracellular matrix.

RCT-1 and RCT-3 are clonal cell lines immortalized by SV-40 large T antigen from cells released from fetal rat calvair by a cmbination collagenase/hyaluronidase digestion. RCT-1 cells, derived from cells released during the first 10 minutes of digestion (fraction I), are cultured in RPMI 1640 medium (BRL) with 10% fetal bovine serum and 0.4 mg/ml G418 (BRL). These cells differentiate and express osteoblastic features upon retinoic acid treatment. RCT-3 cells, immortalized from osteoblast-enriched fraction III cells, are cultured in F-12 medium (BRL) with 5% Fetal bovine serum and 0.4 mg/ml G418. TRAB-11 cells are also immortalized by SV40 large T antigen from adult rat tibia and are cultured in RPMI 1640 medium with 10% FBS and 0.4 mg/ml G418. ROS 17/2.8 rat osteosarcoma cells are cultured in F-12 containing 5% FBS. Osteoblast-enriched (fraction III) primary fetal rat calvaria cells are obtained by collagenase/hyaluronidase digestion of calvariae of 19 day-old rat fetuses. See Rodan et al., *Growth stimulation of rat calvaria osteoblastic cells by acidic FGF, Endocrinology,* 121, 1919–1923 (1987), which is incorporated by reference herein in its entirety. Cells are released during 30–50 minutes digestion (fraction III) and are cultured in F-12 medium containing 5% FBS.

P815 (mouse mastocytoma) cells, cultured in Eagles MEM with 10% FBS, and NRK (normal rat kidney fibroblasts) cells, cultured in DMEM with 10% FBS, are used as positive and negative controls for the expression of $EP_4$, respectively. See Abramovitz et al., *Human prostanoid receptors: cloning and characterization.* In: Samulesson B. et al. ed) *Advances in prostaglandin, Tirombosznes and leukotriene research,* vol. 23, pp. 499–504 (1995) and de Larco et al., *Epithelioid and fibroblastic rat kidney cell clones: EGF receptors and the effect of mouse sarcoma virus transformation, Cell Physiol.,* 94, 335–342 (1978), which are both incorporated by reference herein in their entirety.

3. Northern Blot Analysis:

Total RNA is extracted from the tibial metaphysis or diaphysis and calvaria using a guanidinium isothiocyanate-phenol-chloroform method after pulverizing frozen bone samples by a tissue homogenizer. See P. Chomczynski et al., *Single-step method of RNA isolation by acid guanidium thiocyanate-phenol-chloroform extraction, Analyt Biochem,* 162, 156–159 (1987), which is incorporated by reference herein in its entirety. RNA samples (20 mg) are separated on 0.9% agarose/formaldehyde gels and transferred onto nylon membranes (Boehringer Mannheim, Germany). Membranes are prehybridized in Hybrisol I (Oncor, Gaithersburg, Md.) and 0.5 mg/ml sonicated salmon sperm DNA (Boehringer) at 42° C. for 3 hours and are hybridized at 42° C. with rat $EP_2$ and mouse $EP_4$ cDNA probes labeled with $[^{32}P]$-dCTP (Amersham, Buckinghamshire, UK) by random priming using the rediprime kit (Amersham). After hybridization, membranes are washed 4 times in 2× SSC+0.1% SDS at room temperature for a total of 1 hour and once with 0.2× SSC+0.1% SDS at 55° C. for 1 hour and then exposed to Kodak XAR 2 film at −70° C. using intensifying screens. After developing the films, bound probes are removed twice with 0.1% SDS at 80° C. and membranes are hybridized with a human GAPDH (Glyceraldehyde 3-Phosphate Dehydrogenase) cDNA probe (purchased from Clontech, Palo Alto, Calif.) for loading control.

4. In-Situ Hybridization:

Frozen tibiae are sectioned coronally at 7 mm thickness and sections are mounted on charged slides (Probe On Plus, Fisher Scientific, Springfield, N.J.) and are kept at −70° C. until hybridization. cRNA probes are labeled with $^{35}$S-UTPgS (ICN, Costa Mesa, Calif.) using a Riboprobe II kit (Promega Madison, Wis.). Hybridization is performed overnight at 50° C. See M. Weinreb et al., *Different pattern of alkaline phosphatase, osteopontin and osteocalcin expression in developing rat bone visualized by in-situ hybridization, J. Bone Miner Res.,* 5, 831–842 (1990) and D. Shinar et al., *Expression of alphav and beta3 integrin subunits in rat osteoclasts in situ, J. Bone Miner. Res.,* 8, 403–414 (1993), which are both incorporated by reference herein in their entirety. Following hybridization and washing, sections are dipped in Ilford K5 emulsion diluted 2:1 with 6% glycerol in water at 42° C. and exposed in darkness at 4° C. for 12–14 days. Slides are developed in Kodak D-19 diluted 1:1 with water at 150, fixed, washed in distilled water and mounted with glycerol-gelatin (Sigma) after hematoxylin staining. Stained sections are viewed under the microscope (Olympus, Hamburg, Germany), using either bright-field or dark-field optics.

5. Expression of $EP_4$ in Osteoblastic Cell Lines and in Bone Tissue.

The expression of $EP_4$ and $EP_2$ mRNA is examined in various bone derived cells including osteoblast-enriched primary rat calvaria cells, immortalized osteoblastic cell lines from fetal rat calvaria or from adult rat tibia and an osteoblastic osteosarcoma cell line. Most of the osteoblastic cells and cell lines show significant amounts of 3.8 kb $EP_4$ mRNA, except for the rat osteosarcoma cell line ROS 17/2.8. Consistent with this finding, in ROS 17/2.8 cells $PGE_2$ has no effect on intracellular cAMP, which is markedly induced in RCT-3 and TRAB-11 cells. Treatment of RCT-1 cells with retinoic acid, which promotes their differentiation, reduces the levels of $EP_4$ mRNA. NRK fibroblasts do not express $EP_4$ mRNA, while P815 mastocytoma cells, used as positive controls, express large amounts of $EP_4$ mRNA. In contrast to $EP_4$ mRNA, none of the osteoblastic cells and cell lines express detectable amounts of $EP_2$ mRA in total RNA samples. Expression of $EP_4$ mRNA in osteoblastic cells, $EP_4$ is also expressed in total RNA isolated from tibiae and calvariae of 5-week-old rats. In contrast, no $EP_2$ mRNA is found in RNA from tibial shafts.

6. $PGE_2$ Induces the Expression of $EP_4$ mRNA in RP-1 Periosteal Cells and in Adult Rat Tibiae $PGE_2$ enhances its own production via upregulation of cyclooxygenase 2 expression in osteoblasts and in bone tissue thus autoamplifying its own effects. $PGE_2$ also increases the levels of $EP_4$ mRNA. RP-1 cells are immortalized from a primary culture of adult rat tibia periosteum is examined. These cells express osteoblast phenotypic markers upon confluence and form mineralized bone matrix when implanted in nude mice. Similar to the other osteoblastic cells examined, RP-1 periosteal cells express a 3.8 kb $EP_4$ transcript. Treatment with $PGE_2$ ($10^{-6}$M) rapidly increases $EP_4$ mRNA levels peaking at 2 hours after treatment. $PGE_2$ has no effect on $EP_4$ mRNA levels in the more differentiated RCT-3 cells pointing to cell-type specific regulation of $EP_4$ expression by $PGE_2$. $EP_2$ mRNA is not expressed in RP-1 cells before or after treatment with $PGE_2$.

To examine if $PGE_2$ regulates $EP_4$ mRNA levels in vivo in bone tissue, five-week-old male rats are injected with $PGE_2$ (3–6 mg/Kg). Systemic administration of $PGE_2$ rapidly increased $EP_4$ mRNA levels in the tibial diaphysis peaking at 2 h after injection. A similar effect of $PGE_2$ on $EP_4$ mRNA is observed in the tibial metaphysis and in calvaria. $PGE_2$ induces $EP_4$ mRNA levels in vitro in osteogenic periosteal cells and in vivo in bone tissue in a cell type-specific and tissue-specific manner. $PGE_2$ does not induce $EP_2$ mRNA in RP-1 cells nor in bone tissue.

7. Localization of $EP_4$ mRNA Expression in Bone Tissue

In situ hybridization is used in order to localize cells expressing $EP_4$ in bone. In control experiment (vehicle-injected) rats, low expression of $EP_4$ is detected in bone marrow cells. Administration of a single anabolic dose of $PGE_2$ increased the expression of $EP_4$ in bone marrow cells. The distribution of silver grains over the bone marrow is not uniform and occurs in clumps or patches in many areas of the metaphysis. Within the tibial metaphysis, $EP_4$ expression is restricted to the secondary spongiosa area and is not seen in the primary spongiosa. Hybridization of similar sections with a sense probe (negative control) does not show any signal.

$EP_4$ is expressed in osteoblastic cells in vitro and in bone marrow cells in vivo, and is upregulated by its ligand, $PGE_2$.

8. Agonists Of the Present Invention

Using standard methods for measuring agonist activity, the following compounds are evaluated in cell cultures and in $EP_4$ receptor cell-free systems to determine the agonist activity of the compounds in terms of their $EC_{50}$ value.

What is claimed is:

1. A compound having the structural formula I:

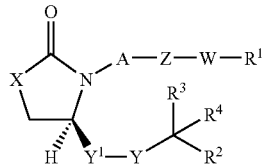

FORMULA I or a pharmaceutically acceptable salt thereof, wherein,

X is S;

$Y^1$ is
1) $CH_2CH_2$, or
2) CHCH;

Y is C(O) or CH(OH);

A and W are independently selected from the group consisting of
1) a bond, and
2) $C_{1-6}$ alkylene, unsubstituted or substituted with 1, 2, 3, or 4 halogen atoms;

Z is
4) $CH_2$,
5) HC=CH, or
6) C≡C;

$R^1$ is
$COR^5$,
OH,
$(CH_2)_{1-3} CO_2R^6$,
$(CH_2)_{0-4} SO_3R^6$,
$CF_2SO_2NH_2$,
$SO_2NH_2$,
$SO_2NHCOR^8$,
$PO(OH)_2$,
$C_{1-4}$ alkoxy,
hydroxymethylketone,
$(CH_2)_{0-4}$ heterocyclyl, wherein heterocyclyl is unsubstituted or substituted with 1 to 3 groups of $R^8$, or
tetrazole;

$R^2$ is
1) $C_{1-6}$alkyl, provided that $R^2$ is not n-pentyl or butyl,
2) $(CH_2)_{0-8}C_{6-10}$aryl,
3) $(CH_2)_{0-8}C_{5-10}$heteroaryl,
4) $(CH_2)_{0-8}C_{3-10}$heterocycloalkyl,
5) $(CH_2)_{0-8}C_{3-8}$cycloalkyl,
6) O—$C_{1-10}$alkyl,
7) O—$C_{6-10}$alkyl,
8) O—$C_{5-10}$heteroaryl,
9) O—$C_{5-10}$heterocycloalkyl, or
10) O—$C_{3-10}$cycloalkyl,
wherein aryl, heteroaryl, heterocycloalkyl, and cycloalkyl are unsubstituted or substituted with 1–3 groups of $R^b$;

$R^3$ and $R^4$ are independently selected from the group consisting of
1) hydrogen,
2) halogen, and
3) $C_{1-6}$ alkyl, or $R^3$ and $R^4$, together with the carbon atom to which they are attached, form a $C_{3-7}$ cycloalkyl ring;

$R^5$ is
1) hydrogen,
2) OH,
3) $CH_2OH$,
4) $C_{1-6}$ alkoxy,
5) $NHPO_2R^6$,
6) $NHR^9$,
7) $NHSO_2R^8$, or
8) $NR^6R^7$;

$R^6$ and $R^7$ are independently selected from the group consisting of hydrogen and $C_{1-6}$alkyl;

$R^8$ is selected from the group consisting of hydrogen, $C_{6-10}$aryl, and $C_{1-4}$alkyl;

$R^9$ is acyl or sulfonyl; and $R^a$ and $R^b$ are independently selected from the group consisting of
1) $C_{1-6}$alkoxy,
2) $C_{1-6}$alkyl, unsubstituted or substituted with
    a) $C_{1-6}$ alkoxy,
    b) $C_{1-6}$ alkylthio,
    c) CN,
    d) OH, or
    e) $CF_3$,
3) $CF_3$,
4) nitro,
5) amino,
6) cyano,
7) $C_{1-6}$alkylamino,
8) halogen
9) $OR^c$,
10) $OCH_2R^c$, and
11) $CH_2OR^c$;

$R^c$ is
1) $C_{6-10}$aryl,
2) $C_{5-10}$heteroaryl,
3) $C_{3-10}$heterocycloalkyl, or
4) $C_{3-8}$cycloalkyl.

2. A compound of claim 1, or a pharmaceutically acceptable salt thereof, wherein $R^2$ is
1) cyclohexyl,
2) unsubstituted aryl, or
3) aryl substituted with
    a) unsubstituted $C_{1-6}$ alkyl,
    b) $C_{1-6}$ alkyl substituted with $C_{1-6}$ alkoxy
    c) halogen, or
    d) $CF_3$.

3. A compound of claim 2, or a pharmaceutically acceptable salt thereof, wherein $R^1$ is tetrazole or $COR^5$, wherein $R^5$ is $CH_2OH$ or OH.

4. A compound of claim 3, or a pharmaceutically acceptable salt thereof, wherein A is a bond, $(CH_2)_{1-4}$, or $(CH_2)_{1-5}CF_2$, and W is a bond or $(CH_2)_{1-6}$.

5. A compound of claim 4, or a pharmaceutically acceptable salt thereof, wherein Z is
1) $CH_2$,
2) CH=CH,
3) C≡C, $R^3$ and $R^4$ are independently selected from the group consisting of hydrogen and F, or $R^3$ and $R^4$, together with the carbon atom to which they are attached, form a cyclopropyl or cyclohexyl ring.

6. A compound of claim 5 selected from the group consisting of
7-{4-[(1E)-4,4-difluoro-3-hydroxy-4-phenylbut-1-enyl]-2-oxo-1,3-thiazolidin-3-yl}heptanoic acid, 7-{4-[(1E)-3-hydroxy-4-phenylbut-1-enyl]-2-oxo-1,3-thiazolidin-3-yl}heptanoic acid, 4-[(1E)-4,4-difluoro-3-hydroxy-4-phenylbut-1-enyl]-3-[6-(1H-tetraazol-5-yl)hexyl]-1,3-thiazolidin-2-one, 4-[(1E)-3-hydroxy-4-phenylbut-1-enyl]-3-[6-(1H-tetraazol-5-yl)hexyl]-1,3-thiazolidin-2-one, 4-[(1E)-3-hydroxy-3-(1-phenylcyclopropyl)prop-1-enyl]-3-[6-(1H-tetraazol-5-yl)hexyl]-1,3-thiazolidin-2-one, 4-(3-hydroxy-4-phenylbutyl)-3-[6-(1H-tetraazol-5-yl)hexyl]-1,3-thiazolidin-2-one, 4-(4,4-difluoro-3-hydroxy-4]phenylbutyl)-3-[6-(1H-tetraazol-5-yl)hexyl]-1,3-thiazolidin-2-one, 7-(4-{(1E)-4,4-difluoro-3-hydroxy-4-[3-(methoxymethyl)phenyl]but-1-enyl}-2-oxo-1,3-thiazolidin-3-yl)heptanoic acid, 4-{(1E)-4,4-difluoro-3-hydroxy-4-[3-(methoxymethyl)phenyl]but-1-enyl}-3-[6-(1H-tetraazol-5-yl)hexyl]-1,3-thiazolidin-2-one, 4-[(1E)-4-cyclohexyl-4,4-difluoro-3-hydroxybut-1-enyl]-3-[6-(1H-tetraazol-5-yl)hexyl]-1,3-thiazolidin-2-one, 4-[(1E)-4-cyclohexyl-3-hydroxybut-1-enyl]-3-[6-(1H-tetraazol-5-yl)hexyl]-1,3-thiazolidin-2-one, 4-(4,4-difluoro-3-oxo-4-phenylbutyl)-3-[6-(1H-tetraazol-5-yl)hexyl]-1,3-thiazolidin-2-one, 4-(3-oxo-4-phenylbutyl)-3-[6-(1H-tetraazol-5-yl)hexyl]-1,3-thiazolidin-2-one, 4-[(1E)-4,4-difluoro-3-hydroxy-4-phenylbut-1-enyl]-3-(7-hydroxy-6-oxoheptyl)-1,3-thiazolidin-2-one, 4-[(1E)-4,4-difluoro-3-hydroxy-4-phenylbut-1-enyl]-3-[(2E)-6-(1H-tetraazol-5-yl)hex-2-enyl]-1,3-thiazolidin-2-one, 4-[(1E)-4,4-difluoro-3-hydroxy-4-phenylbut-1-enyl]-3-[(3E)-6-(1H-tetraazol-5-yl)hex-3-enyl]-1,3-thiazolidin-2-one, 4-[(1E)-4,4-difluoro-3-hydroxy-4-phenylbut-1-enyl]-3-[(4E)-6-(1H-tetraazol-5-yl)hex-2-enyl]-1,3-thiazolidin-2-one, 4-[(1E)-4,4-difluoro-3-hydroxy-4-phenylbut-1-enyl]-3-[(2Z)-6-(1H-tetraazol-5-yl)hex-2-enyl]-1,3-thiazolidin-2-one, 4-[(1E)-4,4-difluoro-3-hydroxy-4-phenylbut-1-enyl]-3-[(3Z)-6-(1H-tetraazol-5-yl)hex-3-enyl]-1,3-thiazolidin-2-one, 4-[(1E)-4,4-difluoro-3-hydroxy-4-phenylbut-1-enyl]-3-[(4Z)-6-(1-tetraazol-5-yl)hex-4-enyl]-1,3-thiazolidin-2-one, 4-[(1E)-4,4-difluoro-3-hydroxy-4-phenylbut-1-enyl]-3-[6-(1H-tetraazol-5-yl)hex-4-ynyl]-1,3-thiazolidin-2-one, 4-[(1E)-4,4-difluoro-3-hydroxy-4-phenylbut-1-enyl]-3-[6-(1H-tetraazol-5-yl)hex-2-ynyl]-1,3-thiazolidin-2-one, 4-[(1E)-4,4-difluoro-3-hydroxy-4-phenylbut-1-enyl]-3-[6-(1H-tetraazol-5-yl)hex-3-ynyl]-1,3-thiazolidin-2-one, 7-{4-[(1E)-4,4-difluoro-3-hydroxy-4-phenylbut-1-yl]-2-oxo-1,3-thiazolidin-3-yl)}-2,2-difluoroheptanoic acid, 7-{4-[(1E)-4,4-difluoro-3-hydroxy-4-phenylbut-1-enyl]-2-oxo-1,3-thiazolidin-3-yl}-4,4-difluoroheptanoic acid, 7-{4-[(1E)-4,4-difluoro-3-hydroxy-4-phenylbut-1-enyl]-2-oxo-1,3-thiazolidin-3-yl}-5,5-difluoroheptanoic acid, 7-{4-[(1E)-4,4-difluoro-3-hydroxy-4-phenylbut-1-enyl]-2-oxo-1,3-thiazolidin-3-yl}-6,6-difluoroheptanoic acid, 7-{4-[(1E)-4,4-difluoro-3-hydroxy-4-phenylbut-1-enyl]-2-oxo-1,3-oxazolidin-3-yl}heptanoic acid, 7-{4-[(1E)-3-hydroxy-4-phenylbut-1-enyl]-2-oxo-1,3-oxazolidin-3-yl}heptanoic acid, 4-[(1E)-4,4-difluoro-3-hydroxy-4-phenylbut-1-enyl]-3-[6-(1H-tetraazol-5-yl)hexyl]-1,3-oxazolidin-2-one, 4-[(1E)-3-hydroxy-4-phenylbut-1-enyl]-3-[6-(1H-tetraazol-5-yl)hexyl]-1,3-oxazolidin-2-one, 4-[(1E)-3-hydroxy-3-(1-phenylcyclopropyl)prop-1-enyl]-3-[6-(1H-tetraazol-5-yl)hexyl]-1,3-oxazolidin-2-one, 4-(3-hydroxy-4-phenylbutyl)-3-[6-(1H-tetraazol-5-yl)hexyl]-1,3-oxazolidin-2-one, 4-(4,4-difluoro-3-hydroxy-4-phenylbutyl)-3-[6-(1H-tetraazol-5-yl)hexyl]-1,3-oxazolidin-2-one, 7-(4-{(1E)-4,4-difluoro-3-hydroxy-4-[3-(methoxymethyl)phenyl]but-1-enyl}-2-oxo-1,3-oxazolidin-3-yl)heptanoic acid, 4-{(1E)-4,4-difluoro-3-hydroxy-4-[3-methoxymethyl)phenyl]but-1-enyl}-3-[6-(1H-tetraazol-5-yl)hexyl]-1,3-oxazolidin-2-one, 4-[(1E)-4-cyclohexyl-4,4-difluoro-3-hydroxybut-1-enyl]-3-[6-(1H-tetraazol-5-yl)hexyl]-1,3-oxazolidin-2-one, 4-[(1E)-4-cyclohexyl-3-hydroxybut-1-enyl]-3-[6-(1H-tetraazol-5-yl)hexyl]-1,3-oxazolidin-2-one, 4-(4,4-difluoro-3-oxo-4-phenylbutyl)-3-[6-(1H-tetraazol-5-yl)hexyl]-1,3-oxazolidin-2-one, 4-(3-oxo-4-phenylbutyl)-3-[6-(1H-tetraazol-5-yl)hexyl]-1,3-oxazolidin-2-one, 4-[(1E)-4,4-difluoro-3-hydroxy-4-phenylbut-1-enyl]-3-(7-hydroxy-6-oxoheptyl)-1,3-oxazolidin-2-one, 4-[(1E)-4,4-difluoro-3-hydroxy-4-phenylbut-1-enyl]-3-[(2E)-6-(1H-tetraazol-5-yl)hex-2-enyl]-1,3-oxazolidin-2-one, 4-[(1E)-4,4-difluoro-3-hydroxy-4-phenylbut-1-enyl]-3-[(3E)-6-(1H-tetraazol-5-yl)hex-3-enyl]-1,3-oxazolidin-2-one, 4-[(1E)-4,4-difluoro-3-hydroxy-4-phenylbut-1-enyl]-3-[(4E)-6-(1H-tetraazol-5-yl)hex-4-enyl]-1,3-oxazolidin-2-one, 4-[(1E)-4,4-difluoro-3-hydroxy-4-phenylbut-1-enyl]-3-[(2Z)-6-(1H-tetraazol-5-yl)hex-2-enyl]-1,3-oxazolidin-2-one, 4-[(1E)-4,4-difluoro-3-hydroxy-4-phenylbut-1-enyl]-3-[(3Z)-6-(1H-tetraazol-5-yl)hex-3-enyl]-1,3-oxazolidin-2-one, 4-[(1E)-4,4-difluoro-3-hydroxy-4-phenylbut-1-enyl]-3-[(4Z)-6-(1H-tetraazol-5-yl)hex-4-enyl]-1,3-oxazolidin-2-one, 4-[(1E)-4,4-difluoro-3-hydroxy-4-phenylbut-1-enyl]-3-[6-(1H-tetraazol-5-yl)hex-4-ynyl]-1,3-oxazolidin-2-one, 4-[(1E)-4,4-difluoro-3-hydroxy-4-phenylbut-1-enyl]-3-[6-(1H-tetraazol-5-yl)hex-2-ynyl]-1,3-oxazolidin-2-one, 4-[(1E)-4,4-difluoro-3-hydroxy-4-phenylbut-1-enyl]-3-[6-(1H-tetraazol-5-yl)hex-3-ynyl]-1,3-oxazolidin-2-one, 7-{4-[(1E)-4,4-difluoro-3-hydroxy-4-phenylbut-1-enyl]-2-oxo-1,3-oxazolidin-3-yl}-2,2-difluoroheptanoic acid, 7-{4-[(1E)-4,4-difluoro-3-hydroxy-4-phenylbut-1-enyl]-2-oxo-1,3-oxazolidin-3-yl}-4,4-difluoroheptanoic acid, 7-{4-[(1E)-4,4-difluoro-3-hydroxy-4-phenylbut-1-enyl]-2-oxo-1,3-oxazolidin-3-yl}-5,5-difluoroheptanoic acid, 7-{4-[(1E)-4,4-difluoro-3-hydroxy-4-phenylbut-1-enyl]-2-oxo-1,3-oxazolidin-3-yl}-6,6-difluoroheptanoic acid, and or a pharmaceutically acceptable salt thereof.

7. A pharmaceutical composition which is comprised of a compound in accordance with claim 1 and a pharmaceutically acceptable carrier.

* * * * *